(12) United States Patent
Ng et al.

(10) Patent No.: US 12,404,312 B2
(45) Date of Patent: Sep. 2, 2025

(54) ENGINEERED VEGF VARIANTS FOR RETINAL NEUROPROTECTION, PROMOTION OF AXON GROWTH AND AXON REGENERATION

(71) Applicant: Massachusetts Eye and Ear Infirmary, Boston, MA (US)

(72) Inventors: Yin Shan Eric Ng, North Billerica, MA (US); Junhui Shen, Hangzhou (CN)

(73) Assignee: Massachusetts Eye and Ear Infirmary, Boston, MA (US)

( * ) Notice: Subject to any disclaimer, the term of this patent is extended or adjusted under 35 U.S.C. 154(b) by 1247 days.

(21) Appl. No.: 16/978,177

(22) PCT Filed: Mar. 5, 2019

(86) PCT No.: PCT/US2019/020744
§ 371 (c)(1),
(2) Date: Sep. 3, 2020

(87) PCT Pub. No.: WO2019/173334
PCT Pub. Date: Sep. 12, 2019

(65) Prior Publication Data
US 2021/0040167 A1 Feb. 11, 2021

Related U.S. Application Data

(60) Provisional application No. 62/638,775, filed on Mar. 5, 2018.

(51) Int. Cl.
*C12P 21/08* (2006.01)
*C07K 7/06* (2006.01)
(Continued)

(52) U.S. Cl.
CPC .............. *C07K 14/475* (2013.01); *C07K 7/06* (2013.01); *C12N 15/86* (2013.01);
(Continued)

(58) Field of Classification Search
None
See application file for complete search history.

(56) References Cited

U.S. PATENT DOCUMENTS

2003/0125295 A1 7/2003 Mintz et al.
2007/0036757 A1 2/2007 Kleinschmidt et al.
(Continued)

FOREIGN PATENT DOCUMENTS

EP 1739092 A1 * 1/2007 ............. A61K 38/00
WO WO-0071716 A2 * 11/2000 ............. A61P 13/12
(Continued)

OTHER PUBLICATIONS

Sheidow et al. Expression of vascular endothelial growth factor in uveal melanoma and its correlation with metastasis, Br J Ophthalmol, Jul. 1, 2000 (Jul. 1, 2000), vol. 84, pp. 750-756. entire document.
(Continued)

*Primary Examiner* — M Franco G Salvoza
(74) *Attorney, Agent, or Firm* — Fish & Richardson P.C.

(57) ABSTRACT

The invention provides methods of promoting retinal ganglion axon formation, survival, and synapse formation.

17 Claims, 11 Drawing Sheets

Specification includes a Sequence Listing.

(51) Int. Cl.
    *C07K 14/475*     (2006.01)
    *C12N 15/86*     (2006.01)

(52) U.S. Cl.
    CPC .... *C07K 2319/02* (2013.01); *C07K 2319/912* (2013.01); *C12N 2710/10041* (2013.01)

(56) References Cited

U.S. PATENT DOCUMENTS

| | | |
|---|---|---|
| 2015/0274793 A1 | 10/2015 | Szkudlinski et al. |
| 2017/0015742 A1 | 1/2017 | Gu et al. |
| 2017/0266243 A1 | 9/2017 | Champion et al. |

FOREIGN PATENT DOCUMENTS

| | | |
|---|---|---|
| WO | WO 2001/076620 | 10/2001 |
| WO | WO 2009/106855 | 9/2009 |
| WO | 2016/115511 A2 | 7/2016 |
| WO | 2017/096124 A1 | 6/2017 |
| WO | 2017/103291 A1 | 6/2017 |

OTHER PUBLICATIONS

Shen et al. "Novel engineered, membrane-localized variants of vascular endothelial growth factor (VEGF) protect retinal ganglion cells: a proof-of-concept study," Cell Death Dis, Oct. 3, 2018 (Oct. 3, 2018), vol. 9, No. 1018, pp. 1-18. entire document.
Written Opinion of the International Searching Authority for International Patent Application No. PCT/US2019/020744 mailed Jun. 26, 2019 (7 pages).
International Search Report for International Patent Application No. PCT/US2019/020744 mailed Jun. 26, 2019 (4 pages).
Altschul et al., "Basic local alignment search tool," J. Mol. Biol., Oct. 1990, 215(3):403-410.
Altschul et al., "Gapped Blast and PSI-Blast: a new generation of protein database search programs," Nuc. Acids Res., Sep. 1977, 25(17):3389-3402.
Chen et al., "Expression of ssDNA in Mammalian Cells," BioTechniques, Jan. 2003, 34:167-171.
Choi et al., "Membrane-Tethered Ligands: Tools for Cell-Autonomous Pharmacological Manipulation of Biological Circuits," Physiology, 2013, 28:164-171.
Ferrara et al., "The biology of VEGF and its receptors," Nat Med, Jun. 2003, 9(6):669-76.
Foxton et al., "Distal retinal ganglion cell axon transport loss and activation of p38 MAPK stress pathway following VEGF-A antagonism," Cell Death Dis, May 2016, 7(5):e2212, 11 pages.
Foxton et al., "VEGF-A is necessary and sufficient for retinal neuroprotection in models of experimental glaucoma," Am J Pathol, Apr. 2013, 182(4):1379-90.
Heider et al., "Biomedical applications of glycosylphosphatidylinositol-anchored proteins," Journal of Lipid Research, 2016, 57:1778-1788.
Henikoff and Henikoff, "Amino acid substitution matrices from protein blocks," Proc. Natl. Acad. Sci. USA, 1992, 89(22):10915-9.
International Preliminary Report on Patentability in International Appln. No. PCT/US2019/020744, mailed on Sep. 17, 2020, 9 pages.
Jin et al., "Vascular endothelial growth factor: direct neuroprotective effect in in vitro ischemia," Proc Natl Acad Sci U S A, Aug. 2000, 97(18):10242-7.
Kim et al., "Constitutive expression of VEGF, VEGFR-1, and VEGFR-2 in normal eyes," Invest Ophthalmol Vis Sci, Aug. 1999, 40(9):2115-21.
Ng et al., "Differential expression of VEGF isoforms in mouse during development and in the adult," Dev Dyn, Feb. 2001, 220(2):112-21.
Nishijima et al., "Vascular endothelial growth factor-A is a survival factor for retinal neurons and a critical neuroprotectant during the adaptive response to ischemic injury," Am J Pathol, Jul. 2007, 171(1):53-67.
Pearson and Lipman, "Improved tools for biological sequence comparison," Proc. Natl. Acad. Sci. USA, May 1988, 85(8):2444-8.
Shen et al. "Abstract: Novel engineered VEGF variant for glaucoma," Abstract, Presented at Proceedings of the 2018 ARVO Annual Meeting, Honolulu, HI, Apr. 29-May 3, 2018, 59:6130, 2 pages.
Smith and Waterman, "Comparison of biosequences," Adv. Appl. Math, Dec. 1981, 2(4):482-489.
Sondell et al., "Vascular endothelial growth factor has neurotrophic activity and stimulates axonal outgrowth, enhancing cell survival and Schwann cell proliferation in the peripheral nervous system," J Neurosci, Jul. 1999, 19(14):5731-40.
Sun et al., "VEGF-induced neuroprotection, neurogenesis, and angiogenesis after focal cerebral ischemia," J Clin Invest, Jun. 2003, 111(12):1843-51.
Tian et al., "Current perspective of neuroprotection and glaucoma," Clin Ophthalmol, Nov. 2015, 9:2109-18.
Weinreb and Medeiros, "The pathophysiology and treatment of glaucoma: a review," JAMA, May 2014, 311(18):1901-11.

* cited by examiner eVEGF-38:
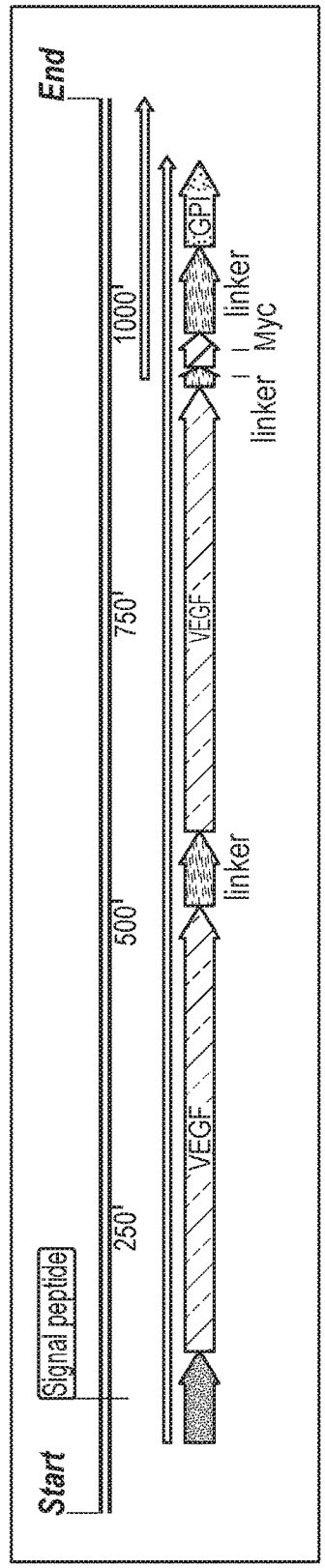
eVEGF-38 amino acid sequence (SEQ ID NO: 1):
MNFLLSWVHWSLALLLYLHHAKWSQAAPMAEGGQNHHEVVKFMDVYQRSYCHPIETLVDIFQEYPDEIEYI
FKPSCVPLMRCGGCCNDEGLECVPTEESNITMQIMRIKPHQGQHIGEMSFLQHNKCECRPKKDRARQEKCDK
PRRGSSGGSGSGGGGTGGGSGAPMAEGGQNHHEVVKFMDVYQRSYCHPIETLVDIFQEYPDEIEYIFKPSC eVEGF-53:

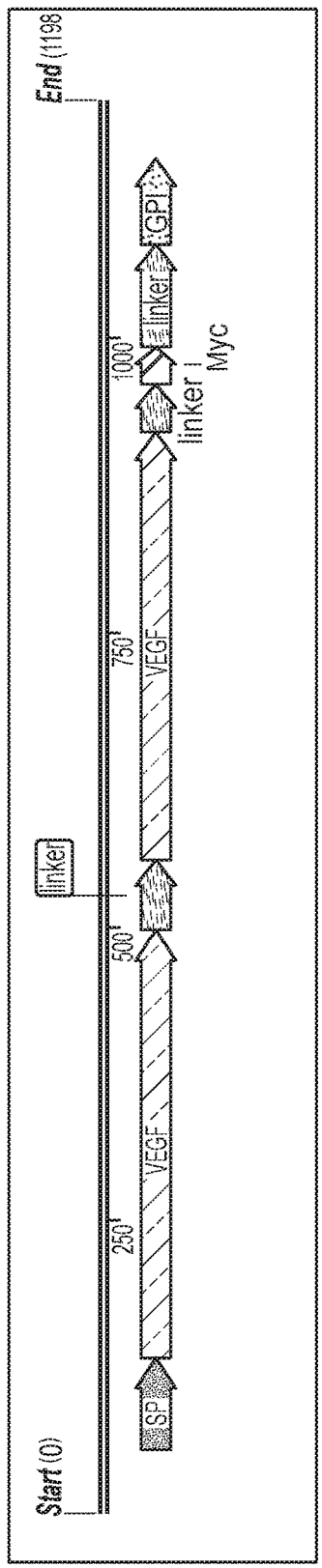

eVEGF-53 amino acid sequence (SEQ ID NO: 2):
MNFLLSWVHWSLALLYLHHAKWSQAAPMAEGGGQNHHEVVKFMDVYQRSYCHPIETLVDIFQEYPDEIEYI
FKPSCVPLMRCGGCCNDEGLECVPTEESNITMQIMRIKPHQGQHIGEMSFLQHNKCECRPKKDRARQEKCDK
PRRGSSGGSSGGGSGGGSGGGTGGGSGAPMAEGGGQNHHEVVKFMDVYQRSYCHPIETLVDIFQEYPDEIEYIFKPSC
VPLMRCGGCCNDEGLECVPTEESNITMQIMRIKPHQGQHIGEMSFLQHNKCECRPKKDRARQEKCDKPRRGN
GNGNGNGNGNGNEQKLIS

VEGF189

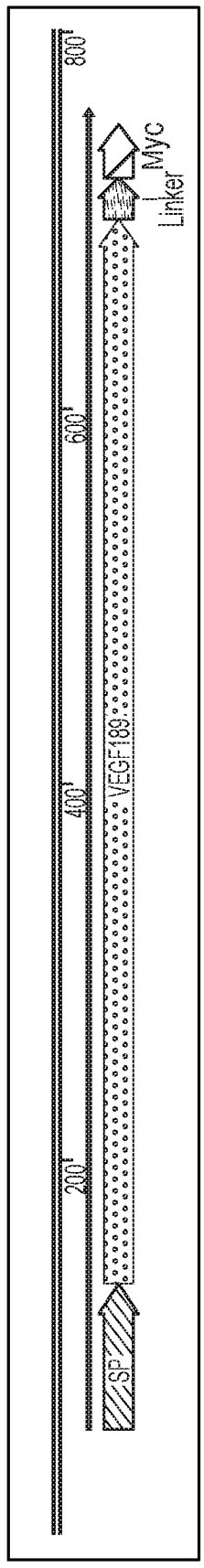

VEGF189 amino acid sequence (SEQ ID NO: 3):
MNFLLSWVHWSLALLLYLHHA:WSQAAPMAEGGGQNHHEVVKFMDVYQRSYCHPIETLVDIFQEYPDEIEYI
FKPSCVPLMRCGGCCNDEGLECVPTEESNITMQIMRIKPHQGQHIGEMSFLQHNKCECRPKKDRARQEKKSVR
GKGKGQKRKKSRYKSWSVPGPCSERRKHLFVQDPQTCKCSCKNTDSRCKARQLELNERTCRCDKPRRKL
GNGNGEQKLISEEDLGN*

Signal peptide (SP) (SEQ ID NO: 12)
Underline: VEGF sequences (189 amino acids) (SEQ ID NO: 19)
flexible linkers (SEQ ID NO: 20)
Myc epitope tag (SEQ ID NO: 16)
strong heparin-binding domain (SEQ ID NO: 21)
Please note that there is a flexible linker (7 amino acids) between the VEGF sequences and the Myc epitope tag ▨ . The strong heparin-binding domain of VEGF189 is highlighted in ▦ .

FIG. 10C

SEQUENCE LISTING

```
<160> NUMBER OF SEQ ID NOS: 21

<210> SEQ ID NO 1
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Cys Asp Lys
        130                 135                 140

Pro Arg Arg Gly Gly Ser Ser Gly Gly Ser Ser Gly Gly Ser Gly Gly
145                 150                 155                 160

Gly Thr Gly Gly Gly Ser Gly Ala Pro Met Ala Glu Gly Gly Gly Gln
                165                 170                 175

Asn His His Glu Val Val Lys Phe Met Asp Val Tyr Gln Arg Ser Tyr
                180                 185                 190

Cys His Pro Ile Glu Thr Leu Val Asp Ile Phe Gln Glu Tyr Pro Asp
            195                 200                 205

Glu Ile Glu Tyr Ile Phe Lys Pro Ser Cys Val Pro Leu Met Arg Cys
        210                 215                 220

Gly Gly Cys Cys Asn Asp Glu Gly Leu Glu Cys Val Pro Thr Glu Glu
225                 230                 235                 240

Ser Asn Ile Thr Met Gln Ile Met Arg Ile Lys Pro His Gln Gly Gln
                245                 250                 255

His Ile Gly Glu Met Ser Phe Leu Gln His Asn Lys Cys Glu Cys Arg
            260                 265                 270

Pro Lys Lys Asp Arg Ala Arg Gln Glu Lys Cys Asp Lys Pro Arg Arg
        275                 280                 285
```

```
Gly Asn Gly Asn Gly Glu Gln Lys Leu Ile Ser Glu Asp Leu Lys
        290                 295                 300

Leu Ala Ala Ala Gly Asn Gly Asn Gly Asn Gly Asp Gly
305                 310                 315                 320

Asn Gly Ala Leu Cys Asn Gly Ala Gly Phe Ala Thr Pro Val Thr Leu
                    325                 330                 335

Ala Leu Val Pro Ala Leu Leu Ala Thr Phe Trp Ser Leu Leu
                340                 345                 350

<210> SEQ ID NO 2
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Cys Asp Lys
130                 135                 140

Pro Arg Arg Gly Gly Ser Ser Gly Gly Ser Ser Gly Gly Ser Gly Gly
145                 150                 155                 160

Gly Thr Gly Gly Gly Ser Gly Ala Pro Met Ala Glu Gly Gly Gly Gln
                165                 170                 175

Asn His His Glu Val Val Lys Phe Met Asp Val Tyr Gln Arg Ser Tyr
            180                 185                 190

Cys His Pro Ile Glu Thr Leu Val Asp Ile Phe Gln Glu Tyr Pro Asp
        195                 200                 205

Glu Ile Glu Tyr Ile Phe Lys Pro Ser Cys Val Pro Leu Met Arg Cys
    210                 215                 220

Gly Gly Cys Cys Asn Asp Glu Gly Leu Glu Cys Val Pro Thr Glu Glu
225                 230                 235                 240

Ser Asn Ile Thr Met Gln Ile Met Arg Ile Lys Pro His Gln Gly Gln
                245                 250                 255

His Ile Gly Glu Met Ser Phe Leu Gln His Asn Lys Cys Glu Cys Arg
            260                 265                 270

Pro Lys Lys Asp Arg Ala Arg Gln Glu Lys Cys Asp Lys Pro Arg Arg
        275                 280                 285

Gly Asn Gly Asn Gly Asn Gly Asn Gly Asn Gly Asn Gly Asn Glu Gln
```

```
              290                 295                 300
Lys Leu Ile Ser Glu Glu Asp Leu Lys Leu Ala Ala Ala Gly Asn Gly
305                 310                 315                 320

Asn Gly Asn Gly Asn Gly Asn Gly Asn Gly Asp Gly Asn Gly
                325                 330                 335

Gly Ala Leu Cys Asn Gly Ala Gly Phe Ala Thr Pro Val Thr Leu Ala
                340                 345                 350

Leu Val Pro Ala Leu Leu Ala Thr Phe Trp Ser Leu Leu
            355                 360                 365

<210> SEQ ID NO 3
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205

Arg Cys Asp Lys Pro Arg Arg Lys Leu Gly Asn Gly Asn Gly Glu Gln
    210                 215                 220

Lys Leu Ile Ser Glu Glu Asp Leu Gly Asn
225                 230

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Val Val Ile Ser Ala Ile Leu Ala Leu Val Val Leu Thr Ile Ile Ser
1               5                   10                  15

Leu Ile Ile Leu Ile
            20

<210> SEQ ID NO 5
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (289)..(341)
<223> OTHER INFORMATION: This region may encompass one of the following
      sequences: "GNGNGEQKLISEEDLKLAAAGNGGNGNGNGDGNGALCN" or
      "GNGNGNGNGNGNGNEQKLISEEDLKLAAAGNGNGNGNGNGNGDGNGGALCN"
<220> FEATURE:
<223> OTHER INFORMATION: See specification as filed for detailed
      description of substitutions and preferred embodiments

<400> SEQUENCE: 5

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Cys Asp Lys
    130                 135                 140

Pro Arg Arg Gly Gly Ser Ser Gly Gly Ser Ser Gly Gly Ser Gly Gly
145                 150                 155                 160

Gly Thr Gly Gly Gly Ser Gly Ala Pro Met Ala Glu Gly Gly Gly Gln
                165                 170                 175

Asn His His Glu Val Val Lys Phe Met Asp Val Tyr Gln Arg Ser Tyr
            180                 185                 190

Cys His Pro Ile Glu Thr Leu Val Asp Ile Phe Gln Glu Tyr Pro Asp
        195                 200                 205

Glu Ile Glu Tyr Ile Phe Lys Pro Ser Cys Val Pro Leu Met Arg Cys
    210                 215                 220

Gly Gly Cys Cys Asn Asp Glu Gly Leu Glu Cys Val Pro Thr Glu Glu
225                 230                 235                 240

Ser Asn Ile Thr Met Gln Ile Met Arg Ile Lys Pro His Gln Gly Gln
                245                 250                 255

His Ile Gly Glu Met Ser Phe Leu Gln His Asn Lys Cys Glu Cys Arg
            260                 265                 270
```

```
Pro Lys Lys Asp Arg Ala Arg Gln Glu Lys Cys Asp Lys Pro Arg Arg
            275                 280                 285

Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Val Val Ile Ser Ala Ile Leu Ala Leu Val Val
                340                 345                 350

Leu Thr Ile Ile Ser Leu Ile Ile Leu Ile
            355                 360

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Leu Ile Thr Ile Ile Ala Met Ser Ala Leu Gly Val Leu Leu Gly
1               5                   10                  15

Ala Val Cys Gly Val Val Leu
            20

<210> SEQ ID NO 7
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (289)..(341)
<223> OTHER INFORMATION: This region may encompass one of the following
      sequences: "GNGNGEQKLISEEDLKLAAAGNGGNGNGNGDGNGALCN" or
      "GNGNGNGNGNGNGNEQKLISEEDLKLAAAGNGNGNGNGNGNGDGNGGALCN"
<220> FEATURE:
<223> OTHER INFORMATION: See specification as filed for detailed
      description of substitutions and preferred embodiments

<400> SEQUENCE: 7

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
            85                  90                  95

Thr Glu Glu Ser Asn Ile Thr Met Gln Ile Met Arg Ile Lys Pro His
        100                 105                 110

Gln Gly Gln His Ile Gly Glu Met Ser Phe Leu Gln His Asn Lys Cys
    115                 120                 125
```

```
Glu Cys Arg Pro Lys Lys Asp Arg Ala Arg Gln Glu Lys Cys Asp Lys
        130                 135                 140
Pro Arg Gly Gly Ser Ser Gly Gly Ser Gly Gly Ser Gly Gly
145                 150                 155                 160
Gly Thr Gly Gly Gly Ser Gly Ala Pro Met Ala Glu Gly Gly Gly Gln
            165                 170                 175
Asn His His Glu Val Val Lys Phe Met Asp Val Tyr Gln Arg Ser Tyr
        180                 185                 190
Cys His Pro Ile Glu Thr Leu Val Asp Ile Phe Gln Glu Tyr Pro Asp
            195                 200                 205
Glu Ile Glu Tyr Ile Phe Lys Pro Ser Cys Val Pro Leu Met Arg Cys
210                 215                 220
Gly Gly Cys Cys Asn Asp Glu Gly Leu Glu Cys Val Pro Thr Glu Glu
225                 230                 235                 240
Ser Asn Ile Thr Met Gln Ile Met Arg Ile Lys Pro His Gln Gly Gln
                245                 250                 255
His Ile Gly Glu Met Ser Phe Leu Gln His Asn Lys Cys Glu Cys Arg
            260                 265                 270
Pro Lys Lys Asp Arg Ala Arg Gln Glu Lys Cys Asp Lys Pro Arg Arg
            275                 280                 285
Xaa Xaa Xaa Xaa Xaa Xaa Xaa Xaa Xaa Xaa Xaa Xaa Xaa Xaa Xaa Xaa
290                 295                 300
Xaa Xaa Xaa Xaa Xaa Xaa Xaa Xaa Xaa Xaa Xaa Xaa Xaa Xaa Xaa Xaa
305                 310                 315                 320
Xaa Xaa Xaa Xaa Xaa Xaa Xaa Xaa Xaa Xaa Xaa Xaa Xaa Xaa Xaa
                325                 330                 335
Xaa Xaa Xaa Xaa Xaa Ile Leu Ile Thr Ile Ile Ala Met Ser Ala Leu
        340                 345                 350
Gly Val Leu Leu Gly Ala Val Cys Gly Val Val Leu
            355                 360

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Ile Ile Leu Val Gly Thr Ala Val Ile Ala Met Phe Phe Trp Leu
1               5                   10                  15

Leu Leu Val Ile Ile
            20

<210> SEQ ID NO 9
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (289)..(341)
<223> OTHER INFORMATION: This region may encompass one of the following
      sequences: "GNGNGEQKLISEEDLKLAAAGNGGNGNGNGDGNGALCN" or
      "GNGNGNGNGNGNEQKLISEEDLKLAAAGNGNGNGNGNGNGDGNGGALCN"
<220> FEATURE:
<223> OTHER INFORMATION: See specification as filed for detailed
      description of substitutions and preferred embodiments
```

<400> SEQUENCE: 9

```
Met Asn Phe Leu Leu Ser Trp Val His Trp Ser Leu Ala Leu Leu Leu
1               5                   10                  15
Tyr Leu His His Ala Lys Trp Ser Gln Ala Ala Pro Met Ala Glu Gly
                20                  25                  30
Gly Gly Gln Asn His His Glu Val Val Lys Phe Met Asp Val Tyr Gln
            35                  40                  45
Arg Ser Tyr Cys His Pro Ile Glu Thr Leu Val Asp Ile Phe Gln Glu
        50                  55                  60
Tyr Pro Asp Glu Ile Glu Tyr Ile Phe Lys Pro Ser Cys Val Pro Leu
65                  70                  75                  80
Met Arg Cys Gly Gly Cys Cys Asn Asp Glu Gly Leu Glu Cys Val Pro
                85                  90                  95
Thr Glu Glu Ser Asn Ile Thr Met Gln Ile Met Arg Ile Lys Pro His
                100                 105                 110
Gln Gly Gln His Ile Gly Glu Met Ser Phe Leu Gln His Asn Lys Cys
            115                 120                 125
Glu Cys Arg Pro Lys Lys Asp Arg Ala Arg Gln Glu Lys Cys Asp Lys
        130                 135                 140
Pro Arg Arg Gly Gly Ser Ser Gly Gly Ser Ser Gly Gly Ser Gly Gly
145                 150                 155                 160
Gly Thr Gly Gly Gly Ser Gly Ala Pro Met Ala Glu Gly Gly Gly Gln
                165                 170                 175
Asn His His Glu Val Val Lys Phe Met Asp Val Tyr Gln Arg Ser Tyr
                180                 185                 190
Cys His Pro Ile Glu Thr Leu Val Asp Ile Phe Gln Glu Tyr Pro Asp
            195                 200                 205
Glu Ile Glu Tyr Ile Phe Lys Pro Ser Cys Val Pro Leu Met Arg Cys
        210                 215                 220
Gly Gly Cys Cys Asn Asp Glu Gly Leu Glu Cys Val Pro Thr Glu Glu
225                 230                 235                 240
Ser Asn Ile Thr Met Gln Ile Met Arg Ile Lys Pro His Gln Gly Gln
                245                 250                 255
His Ile Gly Glu Met Ser Phe Leu Gln His Asn Lys Cys Glu Cys Arg
                260                 265                 270
Pro Lys Lys Asp Arg Ala Arg Gln Glu Lys Cys Asp Lys Pro Arg Arg
            275                 280                 285
Xaa Xaa Xaa Xaa Xaa Xaa Xaa Xaa Xaa Xaa Xaa Xaa Xaa Xaa Xaa Xaa
        290                 295                 300
Xaa Xaa Xaa Xaa Xaa Xaa Xaa Xaa Xaa Xaa Xaa Xaa Xaa Xaa Xaa Xaa
305                 310                 315                 320
Xaa Xaa Xaa Xaa Xaa Xaa Xaa Xaa Xaa Xaa Xaa Xaa Xaa Xaa Xaa Xaa
                325                 330                 335
Xaa Xaa Xaa Xaa Xaa Ile Ile Ile Leu Val Gly Thr Ala Val Ile Ala
            340                 345                 350
Met Phe Phe Trp Leu Leu Leu Val Ile Ile
            355                 360
```

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 10

Val Ala Val Ser Leu Gly Val Gly Leu Ala Val Leu Leu Val Leu Leu
1               5                   10                  15

Gly Met Val Ala Val
            20

<210> SEQ ID NO 11
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (289)..(341)
<223> OTHER INFORMATION: This region may encompass one of the following
      sequences: "GNGNGEQKLISEEDLKLAAAGNGGNGNGNGDGNGALCN" or
      "GNGNGNGNGNGNGNEQKLISEEDLKLAAAGNGNGNGNGNGNGNGDGNGGALCN"
<220> FEATURE:
<223> OTHER INFORMATION: See specification as filed for detailed
      description of substitutions and preferred embodiments

<400> SEQUENCE: 11

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Cys Asp Lys
    130                 135                 140

Pro Arg Arg Gly Gly Ser Ser Gly Gly Ser Gly Gly Ser Gly Gly
145                 150                 155                 160

Gly Thr Gly Gly Gly Ser Gly Ala Pro Met Ala Glu Gly Gly Gly Gln
                165                 170                 175

Asn His His Glu Val Val Lys Phe Met Asp Val Tyr Gln Arg Ser Tyr
            180                 185                 190

Cys His Pro Ile Glu Thr Leu Val Asp Ile Phe Gln Glu Tyr Pro Asp
        195                 200                 205

Glu Ile Glu Tyr Ile Phe Lys Pro Ser Cys Val Pro Leu Met Arg Cys
    210                 215                 220

Gly Gly Cys Cys Asn Asp Glu Gly Leu Glu Cys Val Pro Thr Glu Glu
225                 230                 235                 240

Ser Asn Ile Thr Met Gln Ile Met Arg Ile Lys Pro His Gln Gly Gln
                245                 250                 255

His Ile Gly Glu Met Ser Phe Leu Gln His Asn Lys Cys Glu Cys Arg

```
                260                 265                 270
Pro Lys Lys Asp Arg Ala Arg Gln Glu Lys Cys Asp Lys Pro Arg Arg
        275                 280                 285

Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Val Ala Val Ser Leu Gly Val Gly Leu Ala Val
            340                 345                 350

Leu Leu Val Leu Leu Gly Met Val Ala Val
            355                 360

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Asn Phe Leu Leu Ser Trp Val His Trp Ser Leu Ala Leu Leu Leu
1               5                   10                  15

Tyr Leu His His Ala Lys Trp Ser Gln Ala
            20                  25

<210> SEQ ID NO 13
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Cys Asp Lys Pro Arg Arg
        115                 120

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
                    peptide

<400> SEQUENCE: 14

Gly Gly Ser Ser Gly Gly Ser Ser Gly Gly Ser Gly Gly Gly Thr Gly
1               5                   10                  15

Gly Gly Ser Gly
            20

<210> SEQ ID NO 15
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Asn Gly Asn Gly Glu Gln Lys Leu Ile Ser Glu Glu Asp Leu Lys
1               5                   10                  15

Leu Ala Ala Ala Gly Asn Gly Gly Asn Gly Asn Gly Asn Gly Asp Gly
            20                  25                  30

Asn Gly Ala Leu Cys Asn
        35

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Gln Lys Leu Ile Ser Glu Glu Asp Leu
1               5                   10

<210> SEQ ID NO 17
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Asn Gly Asn Gly Asn Gly Asn Gly Asn Gly Asn Gly Asn Glu Gln
1               5                   10                  15

Lys Leu Ile Ser Glu Glu Asp Leu Lys Leu Ala Ala Ala Gly Asn Gly
            20                  25                  30

Asn Gly Asn Gly Asn Gly Asn Gly Asn Gly Asn Gly Asp Gly Asn Gly
        35                  40                  45

Gly Ala Leu Cys Asn
    50

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ala Gly Phe Ala Thr Pro Val Thr Leu Ala Leu Val Pro Ala Leu
```

```
1               5                   10                  15
Leu Ala Thr Phe Trp Ser Leu Leu
                20

<210> SEQ ID NO 19
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
        50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
                100                 105                 110

Gln Glu Lys Lys Ser Val Arg Gly Lys Gly Lys Gly Gln Lys Arg Lys
            115                 120                 125

Arg Lys Lys Ser Arg Tyr Lys Ser Trp Ser Val Pro Cys Gly Pro Cys
        130                 135                 140

Ser Glu Arg Arg Lys His Leu Phe Val Gln Asp Pro Gln Thr Cys Lys
145                 150                 155                 160

Cys Ser Cys Lys Asn Thr Asp Ser Arg Cys Lys Ala Arg Gln Leu Glu
                165                 170                 175

Leu Asn Glu Arg Thr Cys Arg Cys Asp Lys Pro Arg Arg
            180                 185

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Leu Gly Asn Gly Asn Gly
1               5

<210> SEQ ID NO 21
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Lys Lys Ser Val Arg Gly Lys Gly Lys Gly Gln Lys Arg Lys Arg Lys
1               5                   10                  15
```

-continued

```
Lys Ser Arg Tyr Lys Ser Trp Ser Val Pro Cys Gly Pro Cys Ser Glu
            20              25              30

Arg Arg Lys His Leu Phe Val Gln Asp Pro Gln Thr Cys Lys Cys Ser
            35              40              45

Cys Lys Asn Thr Asp Ser Arg Cys Lys Ala Arg Gln Leu Glu Leu Asn
    50              55              60

Glu Arg Thr Cys Arg Cys Arg
65              70
```

ENGINEERED VEGF VARIANTS FOR RETINAL NEUROPROTECTION, PROMOTION OF AXON GROWTH AND AXON REGENERATION

CROSS REFERENCE TO RELATED APPLICATIONS

This application is a U.S. national stage application filed under 35 U.S.C. § 371 of International Patent Application No. PCT/US19/20744, filed Mar. 5, 2019, which claims the benefit of priority under 35 U.S.C. § 119 (e) to U.S. Provisional Application No. 62/638,775 filed Mar. 5, 2018, the entire contents of which is incorporated herein by reference.

SEQUENCE LISTING

The instant application contains a Sequence Listing which has been submitted electronically in ASCII format and is hereby incorporated by reference in its entirety. Said ASCII copy, created on Apr. 11, 2019, is named 036770-573001WO_SL.txt and is 30,832 bytes in size.

FIELD OF THE INVENTION

The present invention relates to ocular disorders.

BACKGROUND

Glaucoma can damage the optic nerve, which ultimately leads to the degeneration of the retinal ganglion cells (RGC), a leading cause of irreversible blindness in working-age adults. Currently, there is no effective treatment for glaucoma.

SUMMARY OF THE INVENTION

The invention represents a solution for major unmet medical need in the field of ophthalmology. Accordingly, the invention provides compositions, e.g., an engineered Vascular endothelial growth factor (VEGF) chimeric polypeptide, comprising a flexible transmembrane anchor such as a chimeric polypeptide comprising a polypeptide linker with a length of 38-53 amino acids, inclusive. Exemplary chimeric polypeptides include e-VEGF-38, eVEGF-53. A retinal ganglion cell (RGC) comprising a membrane anchored VEGF polypeptide is also within the invention.

The compositions are useful to confer clinical benefit to individuals in need of neuroprotection. For example, a method of neuroprotection and promoting RGC survival and axon formation, is carried out by contacting a RGC of a subject with a construct expressing the chimeric polypeptide (s) described above. In some examples, the subject is diagnosed with glaucoma. The methods are associated with significant advantages over earlier approaches to ocular neuroprotection, because the constructs preferentially promote cell autologous VEGF signaling, thereby avoiding undesirable effects caused by VEGF acting on bystander cells.

In certain embodiments, an engineered or recombinant vascular endothelial growth factor (VEGF) chimeric polypeptide comprises: a flexible transmembrane anchor, a first polypeptide linker, a first VEGF polypeptide covalently linked to a second VEGF polypeptide via a the first polypeptide linker, a second polypeptide linker covalently linking the second VEGF polypeptide to the flexible transmembrane anchor. In certain embodiments, the flexible transmembrane anchor is a glycosylphosphatidylinisotol (GPI) anchor. In certain embodiments, the first and second polypeptide linkers are flexible. In certain embodiments, the polypeptide linkers comprise about 10 amino acids to about 80 amino acids. In certain embodiments, the second polypeptide linker comprises about 20 to about 50 amino acids. In certain embodiments, the second polypeptide linker comprises about 25 to about 45 amino acids. In certain embodiments, the second polypeptide linker comprises about 30 to about 40 amino acids. In certain embodiments, the second polypeptide linker comprises about 53 amino acids. In certain embodiments, the second polypeptide linker comprises about 38 amino acids. In certain embodiments, the first polypeptide linker comprises about 5 to about 40 amino acids. In certain embodiments, the first polypeptide linker comprises about 10 to about 35 amino acids. In certain embodiments, the first polypeptide linker comprises about 15 to about 25 amino acids. In certain embodiments, the first polypeptide linker comprises about 20 amino acids. In certain embodiments, a signal peptide is linked to the N-terminal end of the first VEGF polypeptide. In certain embodiments, the first and second VEGF polypeptides comprise about 100 amino acids to about 200 amino acids. In certain embodiments, the first and second VEGF polypeptides comprise about 121 amino acids. In certain embodiments, the second polypeptide linker optionally comprises a tag epitope. In certain embodiments, the first and/or second VEGF polypeptide comprise: isoforms of VEGF, mutants, chimeric polypeptides, derivatives, active fragments or combinations thereof. In certain embodiments, the first and second VEGF polypeptides are VEGF isoforms comprising 121 amino acids. In certain embodiments, the VEGF isoform comprises the amino acid sequence set forth as SEQ ID NO: 13. In certain embodiments, the first polypeptide linker comprises an amino sequence SEQ ID NO: 14. In certain embodiments, the second polypeptide linker comprises SEQ ID NO: 15 or 17. In certain embodiments, the flexible transmembrane anchor comprises SEQ ID NO: 18.

In certain embodiments, an engineered or recombinant vascular endothelial growth factor (VEGF) chimeric polypeptide comprises: a signal peptide linked to the N-terminal end of a VEGF polypeptide which is covalently linked via a first polypeptide linker to a second VEGF polypeptide which is covalently linked to a flexible transmembrane anchor. In certain embodiments the first polypeptide linker comprises 7 amino acids and the second polypeptide linker comprises 38 amino acids. In certain embodiments, the first polypeptide linker comprises 7 amino acids and the second polypeptide linker comprises 53 amino acids.

In certain embodiments, an engineered or recombinant vascular endothelial growth factor (VEGF) chimeric polypeptide comprises: a signal peptide linked to the N-terminal end of a VEGF polypeptide which is covalently linked to a polypeptide linker. In certain embodiments, the VEGF polypeptide comprises 189 amino acids inclusive of a strong heparin-binding domain.

In certain embodiments, a pharmaceutical composition comprises any one or more of the recombinant vascular endothelial growth factor (VEGF) chimeric polypeptide embodied herein.

In certain embodiments, an engineered or recombinant vascular endothelial growth factor (VEGF) chimeric polypeptide comprises: a sequence identity that is at least about 60% identical to SEQ ID NOS: 1, 2, 3, 5, 7, 9 or 11 over the entire length of SEQ ID NOS: 1, 2, 3, 5, 7, 9 or 11.

In certain embodiments, an engineered or recombinant vascular endothelial growth factor (VEGF) chimeric polypeptide comprises: a signal peptide linked to the N-terminal end of a VEGF polypeptide which is covalently linked via a first polypeptide linker to a second VEGF polypeptide which is covalently linked to a flexible transmembrane anchor, encoded by SEQ ID NOS: 1, 2, 5, 7, 9, 11 or variants thereof, having at least about 70% (such as at least about 75%, 80%, 85%, 90%, 91%, 92%, 93%, 94%, 95%, 96%, 97%, 98%, 99%, or greater) sequence identity thereto. For example, in some embodiments, the engineered or recombinant vascular endothelial growth factor (VEGF) chimeric polypeptide comprising the amino acid sequence of SEQ ID NO: 1, 2, 5, 7, 9 or 11, comprises a signal peptide, such as the signal peptide amino acid sequence of SEQ ID NO: 12 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NOS: 1, 2, 5, 7, 9 or 11, comprises a VEGF polypeptide, such as the VEGF polypeptide comprising the amino acid sequence of SEQ ID NO: 13 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NOS: 1, 2, 5, 7, 9 or 11, comprises a first polypeptide linker, such as the first polypeptide linker comprising the amino acid sequence of SEQ ID NO: 14 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NOS: 1, 2, 5, 7, 9 or 11, comprises a second polypeptide linker, such as the second polypeptide linker comprising the amino acid sequence of SEQ ID NO: 17 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NOS: 1, 2, 5, 7, 9 or 11, comprises a flexible transmembrane anchor, such as the flexible transmembrane anchor comprising the amino acid sequence of SEQ ID NO: 18 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NOS: 1, 2, 5, 7, 9 or 11, comprises a flexible transmembrane anchor, such as the flexible transmembrane anchor comprising the amino acid sequence of SEQ ID NO: 4 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NOS: 1, 2, 5, 7, 9 or 11, comprises a flexible transmembrane anchor, such as the flexible transmembrane anchor comprising the amino acid sequence of SEQ ID NO: 7 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NOS: 1, 2, 5, 7, 9 or 11, comprises a flexible transmembrane anchor, such as the flexible transmembrane anchor comprising the amino acid sequence of SEQ ID NO: 8 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NOS: 1, 2, 5, 7, 9 or 11, comprises a flexible transmembrane anchor, such as the flexible transmembrane anchor comprising the amino acid sequence of SEQ ID NO: 10 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NOS: 1, 2, 5, 7, 9 or 11, comprises a Myc epitope tag, such as the Myc epitope tag comprising the amino acid sequence of SEQ ID NO: 16 or a variant thereof having at least about 70% (such as at least about 75%, 80%, 85%, 90%, 91%, 92%, 93%, 94%, 95%, 96%, 97%, 98%, 99%, or greater) sequence identity thereto.

In certain embodiments, the VEGF chimeric polypeptide comprises SEQ ID NOS: 1, 2, 3, 5, 7, 9 or 11.

In certain embodiments, an engineered or recombinant vascular endothelial growth factor (VEGF) chimeric polypeptide comprises a VEGF polypeptide, a flexible peptide linker wherein the VEGF polypeptide comprises a heparin binding domain. In certain embodiments, the flexible peptide linker comprises about 2 amino acids to about 20 amino acids. In certain embodiments, the flexible peptide linker comprises about 4 amino acids to about 15 amino acids. In certain embodiments, the flexible peptide linker comprises about 7 amino acids. In certain embodiments, the VEGF polypeptide comprises about 100 amino acids to about 250 amino acids. In certain embodiments, the VEGF polypeptide comprises about 120 amino acids to about 200 amino acids. In certain embodiments, the VEGF polypeptide comprises about 140 amino acids to about 190 amino acids. In certain embodiments, the VEGF polypeptide comprises about 189 amino acids.

In certain embodiments, an engineered or recombinant vascular endothelial growth factor (VEGF) chimeric polypeptide comprises a sequence identity that is at least about 60% identical to SEQ ID NO: 3 over the entire length of SEQ ID NO: 3.

In certain embodiments, an engineered or recombinant vascular endothelial growth factor (VEGF) chimeric polypeptide comprises a VEGF polypeptide, a flexible peptide linker wherein the VEGF polypeptide comprises a heparin binding domain, encoded by SEQ ID NO: 21 or variants thereof, having at least about 70% (such as at least about 75%, 80%, 85%, 90%, 91%, 92%, 93%, 94%, 95%, 96%, 97%, 98%, 99%, or greater) sequence identity thereto. For example, in some embodiments, the engineered or recombinant vascular endothelial growth factor (VEGF) chimeric polypeptide comprising the amino acid sequence of SEQ ID NO: 3, comprises a signal peptide, such as the signal peptide amino acid sequence of SEQ ID NO: 12 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NOS: 3, comprises a VEGF polypeptide, such as the VEGF polypeptide comprising the amino acid sequence of SEQ ID NO: 19 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NO: 3, comprises a polypeptide linker, such as the polypeptide linker comprising the amino acid sequence of SEQ ID NO: 20 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NO: 3, comprises a strong heparin-binding domain, such as the strong heparin-binding domain comprising the amino acid sequence of SEQ ID NO: 21 or a variant thereof having at least about 70% (such as at least about 75%, 80%, 85%, 90%, 91%, 92%, 93%, 94%, 95%, 96%, 97%, 98%, 99%, or greater) sequence identity thereto.

In some embodiments, the engineered or recombinant vascular endothelial growth factor (VEGF) chimeric polypeptide comprising the amino acid sequence of SEQ ID NO: 3, comprises a Myc epitope tag, such as the Myc epitope tag comprising the amino acid sequence of SEQ ID NO: 16 or a variant thereof having at least about 70% (such as at least about 75%, 80%, 85%, 90%, 91%, 92%, 93%, 94%, 95%, 96%, 97%, 98%, 99%, or greater) sequence identity thereto.

In certain embodiments, a pharmaceutical composition comprising an engineered or recombinant vascular endothelial growth factor (VEGF) chimeric polypeptide embodied herein.

In certain embodiments, a flexible transmembrane anchor comprises any one of SEQ ID NOS: 4, 6, 8, 10 or 18.

In certain embodiments, an expression vector comprising an isolated nucleic acid encoding any one of SEQ ID NOS: 1-21 or combinations thereof. In certain embodiments, an expression vector is an adenovirus vector, an adeno-associated viral vector (AAV), or derivatives thereof. In certain embodiments, the adeno-associated viral vector comprises AAV serotypes 1, 2, 3, 4, 5, 6, 7, 8, 9, 10, 11, DJ or DJ/8. In certain embodiments, the adeno-associated viral vector is AAV serotype 2 (AAV2). In certain embodiments, the vector encodes for SEQ ID NO: 1, 2, 3, 5, 7, 9 or 11.

In certain embodiments, a retinal ganglion cell (RGC) comprises a membrane anchored vascular endothelial growth factor (VEGF) polypeptide. In certain embodiments, the VEGF polypeptide comprises a flexible transmembrane anchor, a first polypeptide linker, a first VEGF polypeptide covalently linked to a second VEGF polypeptide via a second polypeptide linker. In certain embodiments, the flexible transmembrane anchor is a glycosylphosphatidylinisotol (GPI) anchor. In certain embodiments, the VEGF polypeptide comprises SEQ ID NO: 1, 2, 5, 7, 9 or 11. In certain embodiments, a non-anchored VEGF polypeptide comprises SEQ ID NO: 3.

In certain embodiments, a stem cell comprises SEQ ID NO: 1, 2, 5, 7, 9 or 11.

In certain embodiments, a method of promoting retinal ganglion cell (RGC) axon formation comprises contacting an RGC of a subject with an expression vector expressing the vascular endothelial growth factor (VEGF) chimeric polypeptide embodied herein. In certain embodiments, the subject is diagnosed with glaucoma.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

DESCRIPTION OF THE DRAWINGS

FIG. 7A shows that overexpression of eVEGF-38, eVEGF-53, and VEGF189 significantly increases the percentage of RGC with axons longer than 3× cell body length, the average axon length per RGC, the average number of neurites per RGC compared to the GFP control. Overexpression of eVEGF-38 and eVEGF-53 also significantly increase the average number of branch points of neurite per RGC compared to control. Recombinant VEGF121 protein was added to a final concentration of 2.5 nM. FIG. 7B shows that VEGFR2 inhibitor sunitinib completely inhibits the effect of eVEGF's and VEGF189 on neurite formation in primary RGC. Labels: 38, eVEGF-38; 53, eVEGF-53; 189, VEGF189; UT, untreated. Data=mean±SD, n=15 fields from 3 independent wells per group, *P<0.05, P<0.01, *P<0.001, one-way ANOVA.

FIG. 10A is a diagram showing the organization and sequence of eVEGF-38 (SEQ ID NO: 1).
Signal peptide (SEQ ID NO: 12):

MNFLLSWVHWSLALLLYLHHAKWSQA

Figure 1A:
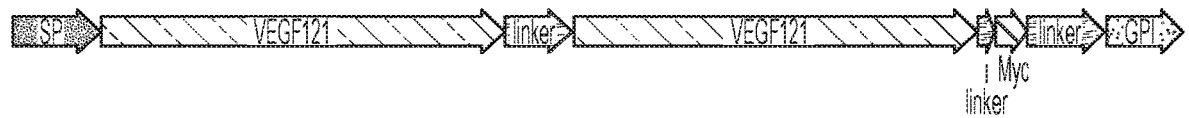
FIG. 1A is a diagram of the design of eVEGF-38 and eVEGF-53 chimeric polypeptides, which are engineered covalently linked dimers of VEGF121 isoform, with a 38 and a 53 glycine-rich amino acids linker, respectively, connected to a GPI anchor at the C-terminus of the polypeptides. SP=Signal peptide; Myc=Myc epitope tag.

VEGF121 (SEQ ID NO: NO 13):

APMAEGGGQNHHEVVKFMDVYQRSYCHPIETLVDIFQEYPDEIEYIFKPS

CVPLMRCGGCCNDEGLECVPTEESNITMQIMRIKPHQGQHIGEMSFLQHN

KCECRPKKDRARQEKCDKPRR

First polypeptide linker (SEQ ID NO: 14):

GGSSGGSSGGSGGGTGGGSG

Second polypeptide (38 amino acid) linker (SEQ ID NO: 15):

GNGNGEQKLISEEDLKLAAAGNGGNGNGNGDGNGALCN

Myc tag (SEQ ID NO: 16):

EQKLISEEDL

GPI anchor (SEQ ID NO: 18):

GAGFATPVTLALVPALLATFWSLL.

FIG. 10B is a diagram showing the organization and sequence of eVEGF-53 (SEQ ID NO: 2).
Signal peptide (SEQ ID NO: 12):

MNFLLSWVHWSLALLLYLHHAKWSQA

VEGF121 (SEQ ID NO: NO 13):

APMAEGGGQNHHEVVKFMDVYQRSYCHPIETLVDIFQEYPDEIEYIFKPS

CVPLMRCGGCCNDEGLECVPTEESNITMQIMRIKPHQGQHIGEMSFLQHN

KCECRPKKDRARQEKCDKPRR

First polypeptide linker (SEQ ID NO: 14):

GGSSGGSSGGSGGGTGGGSG

Second polypeptide linker (53 amino acids); SEQ ID NO: 17):

GNGNGNGNGNGNGNEQKLISEEDLKLAAAGNGNGNGNGNGNGNGDGNGGA
LCN

Myc tag (SEQ ID NO: 16):

EQKLISEEDL

GPI anchor (SEQ ID NO: 18):

GAGFATPVTLALVPALLATFWSLL.

FIG. 10C is a diagram showing the organization and sequence of eVEGF189 (SEQ ID NO: 3).
Signal peptide (SEQ ID NO: 12):

MNFLLSWVHWSLALLLYLHHAKWSQA

VEGF189 (SEQ ID NO: 19):

APMAEGGGQNHHEVVKFMDVYQRSYCHPIETLVDIFQEYPDEIEYIFKPSC
VPLMRCGGCCNDEGLECVPTEESNITMQIMRIKPHQGQHIGEMSFLQHNKC
ECRPKKDRARQEKKSVRGKGKGQKRKRKKSRYKSWSVPCGPCSERRKHLFV
QDPQTCKCSCKNTDSRCKARQLELNERTCRCDKPRR

Flexible linker (SEQ ID NO: 20):

KLGNGNG

Myc tag (SEQ ID NO: 16):

EQKLISEEDL

Heparin binding domain (SEQ ID NO: 21):

KKSVRGKGKGQKRKRKKSRYKSWSVPCGPCSERRKHLFVQDPQTCKCSCKN
TDSRCKARQLELNERTCRCR.

DETAILED DESCRIPTION

VEGF is a signaling protein that promotes the growth of new blood vessels. The invention features a method of preventing retinal ganglion cell ("RGC") degeneration by expressing a membrane anchored VEGF construct ("VEGF/GPI construct") on RGCs.

VEGF has pro-angiogenic, pro-vascular permeability, pro-inflammatory, and neuroprotective activities. Membrane anchored VEGF constructs, e.g., eVEGF-38 and eVEGF-53, were made. These membrane anchored VEGF constructs can be targeted to RGCs via gene therapy and functional mRNA. VEGF tethered to an RGC protects that RGC, cell autonomously. Since the VEGF is tethered, it minimizes or reduces action on other types of cells to promote angiogenesis, vascular permeability and inflammation, which are undesirable. In addition, eVEGF-38 and eVEGF-53 promote synapse formation and axon regeneration.

eVEGF-38 and eVEGF-53 have 38- and 53-residue linkers respectively, and similar constructs have linkers with 39 to 52 residues. Constructs such as these are useful for the treatment of glaucoma. Optionally, the constructs may be administered to subjects that are also receiving other medications, e.g., Rhopressa and Roclatan (both from Aerie Pharmaceuticals), latanoprostene bunod (Vesneo; Bausch+Lomb), and trabodenoson (Inotek Pharmaceuticals) as well as fixed-dose combination products such as tafluprost and timolol maleate (Tapcom; Santen), tafluprost and timolol (Taptiqom; Santen) and brimonidine and brinzolamide (Simbrinza; Alcon).

Retinal Neuroprotection and Promotion of Axon Growth or Regeneration

Because of the multi-factorial nature of glaucoma, developing effective treatments for this complex pathology by targeting genes and pathways that are implicated in the pathogenesis has been proven to be challenging. Vascular endothelial growth factor (VEGF) can act a potent neuroprotectant for the retinal neurons, and especially RGC, and more importantly that RGC express VEGF receptor 2 (VEGFR2), and also produce and use endogenous VEGF to protect themselves from stress-induced cell death, including that of ocular hypertensive (OHT) glaucoma. These findings support VEGF as an endogenous neuroprotectant.

Figure 1B:
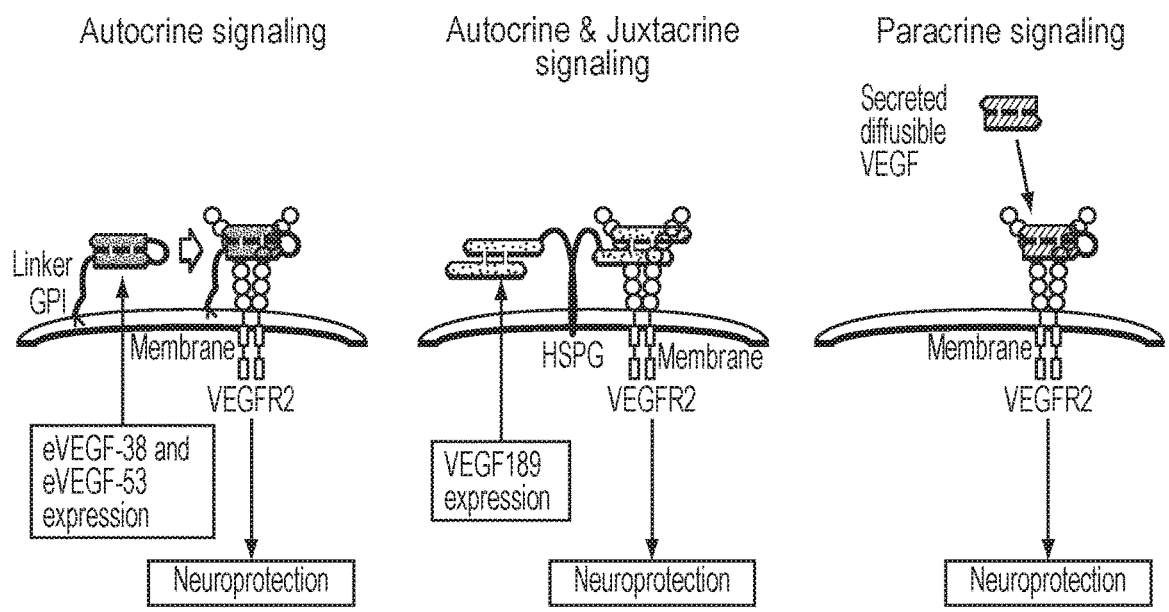
FIG. 1B is a series of diagrams showing mechanism(s) of action for the membrane tethered eVEGF variants and the VEGF198 isoform mediated neuroprotection by autocrine and juxtacrine VEGFR2 signaling, which is distinct from the paracrine signaling by the native VEGF as a secreted and diffusible growth factor. These figures show the design of the membrane-tethered engineered VEGF variants and their cell-autonomous mechanism of action in neuroprotection.

VEGF is a secreted and diffusible factor and thus can also induce unwanted blood vessel growth, permeability and vascular inflammation in the retina. In order to avoid these unwanted effects, engineered VEGF chimeric polypeptides (e.g., eVEGF-38 and eVEGF-53) were developed. These chimeric polypeptides are both engineered covalently linked dimers of VEGF121 isoform tethered to the plasma membrane via a glycophosphatidylinositol (GPI) anchor (FIG. 1A). Therefore these engineered VEGF chimeric polypeptides protect mainly the RGCs expressing them (via autocrine signaling) and likely the neighboring RGC that are in direct cell-cell contact (FIG. 1B). In this way, these novel engineered VEGF chimeric polypeptides will be available only to the RGC overexpressing them to prevent or limit any off target effects. VEGF action on other non RGC cells is therefore minimized or eliminated.

For comparison, also tested was the natural VEGF189 isoform, which binds tightly to heparan sulfate proteoglycan (HSPG) on the cell surface and extracellular matrix that once secreted the VEGF189 proteins are mostly available locally (via autocrine and juxtacrine signaling) (FIG. 1B). The VEGF189 isoform was overexpressed to compare with the novel engineered VEGF chimeric polypeptides in their ability for protecting RGC.

Figure 2A:
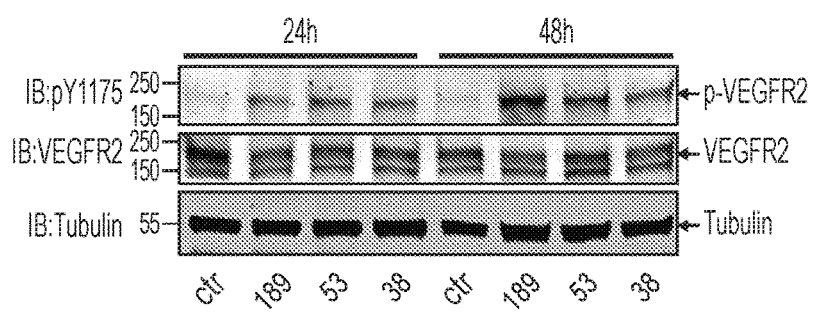
FIG. 2A is a photograph of an electrophoretic gel and FIG. 2B is a bar graph showing that eVEGF-38 and eVEGF-53, and VEGF189 are functional and can sustain VEGFR2 activation in a cell autonomous fashion. Human retinal endothelial cells (hREC) that express VEGFR2 were transfected with eVEGF-38 or eVEGF-53, or VEGF189, or control GFP (ctr) expression construct and total cell lysate was collected at 24 and 48 hours post transfection. Activation of VEGFR2 was determined by the levels of VEGFR2 phosphorylation (p-VEGFR2). Data=mean±SD, **P<0.01 by unpaired t-test, n=3 independent western blot assays.
Figure 2B:
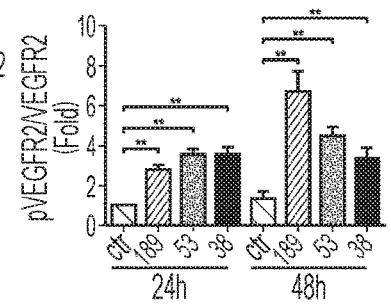
Figure 3A:
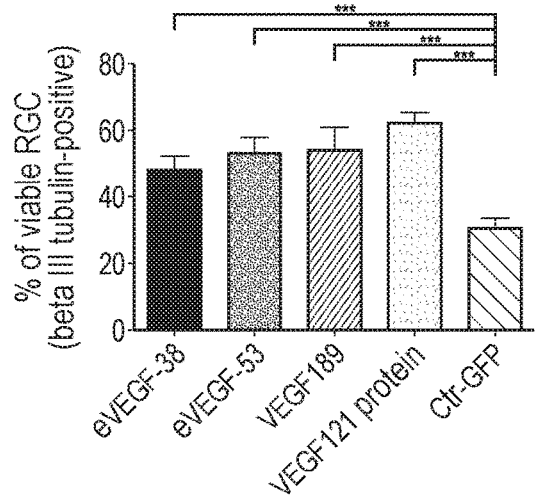
FIG. 3A is a bar graph showing the results from experiments using primary mouse RGC isolated from P3 pups were transduced with different AAVs to overexpress eVEGF-38, eVEGF-53, VEGF189, or the control GFP on the day of isolation (day 0), or treated with exogenous recombinant VEGF121 protein on day 2. The number viable RGC was determined by immunostaining for beta III tubulin while total cell number per field was determined by DAPI staining on day 3 of culture.
Figure 3B:
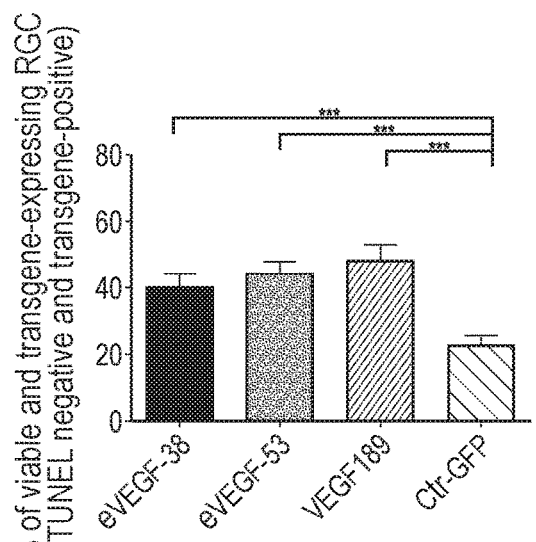
FIG. 3B is a bar graph showing that the majority of the viable RGC were expressing the eVEGF-38, eVEGF-53, or VEGF189, whereas the GFP-expressing RGC were not protected in culture. Data=mean±SD, ***P<0.001 by unpaired t-test, n=15 different fields total (5 fields/well) from three independent wells of primary RGC. These figures demonstrate that overexpression of eVEGF-38, eVEGF-53, or VEGF189 significantly protect primary mouse RGC in culture in a cell autonomous fashion compared to GFP control, and with similar efficacy as exogenous VEGF121 protein treatment.
Figure 4A:
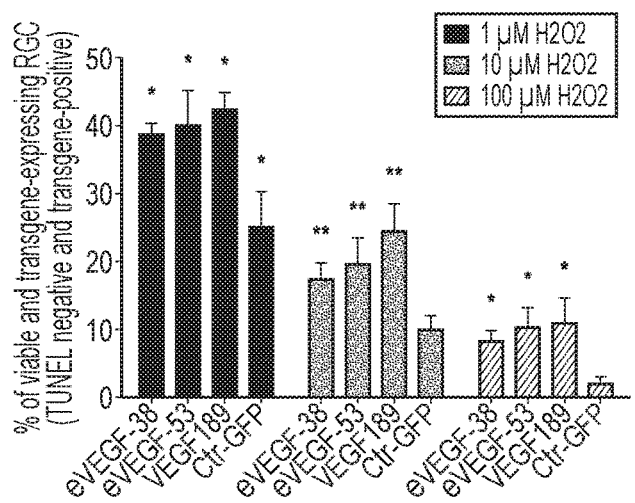
FIG. 4A is a bar graph showing the results from experiments using primary mouse RGC that were treated with different concentrations of $H_2O_2$ for 5 hours. Cell death was analyzed by TUNEL staining and transgene expression by immunostaining. Percentage of viable RGC was determined by: (TUNEL-negative RGC with transgenes expression)/(total cell number by DAPI staining).
Figure 4B:
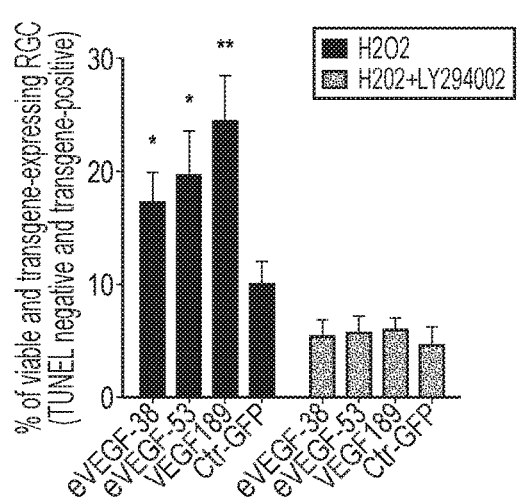
FIG. 4B is a bar graph showing that treatment with PI3K inhibitor LY294002 abolished the protective effects of eVEGFs and VEGF189 against 10 μM $H_2O_2$. Data=mean±SD, n=15 different fields total from three independent wells of primary RGC, *P<0.05, **P<0.01 compared to corresponding GFP control by unpaired t-test. These figures demonstrate that overexpression of eVEGF-38, eVEGF-53, or VEGF189 significantly protect primary mouse RGC from $H_2O_2$-induced cell death in a cell autonomous fashion by activation of the phosphoinositide 3-kinases (PI3K) pathway compared to GFP control.
Figure 5A:
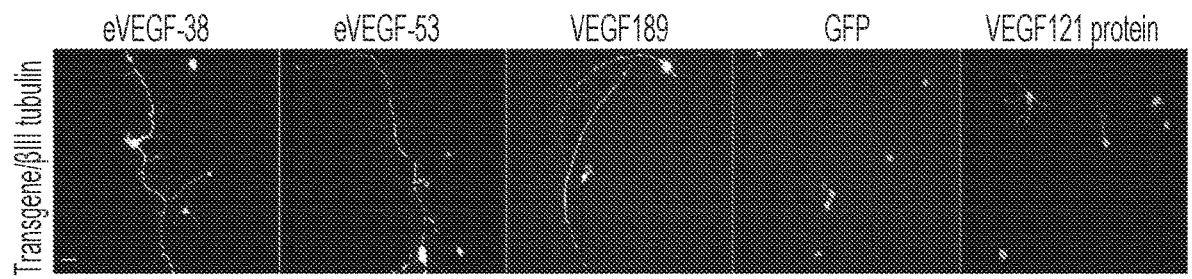
FIG. 5A is a series of photomicrographs showing long axons formation in primary mouse RGC overexpressing eVEGF-38, eVEGF-53, and VEGF189, but not in the GFP-overexpressing control, whereas treatment with soluble recombinant VEGF121 protein did not promote long axons formation even at high concentration. Bar=20 μm.
Figure 5B:
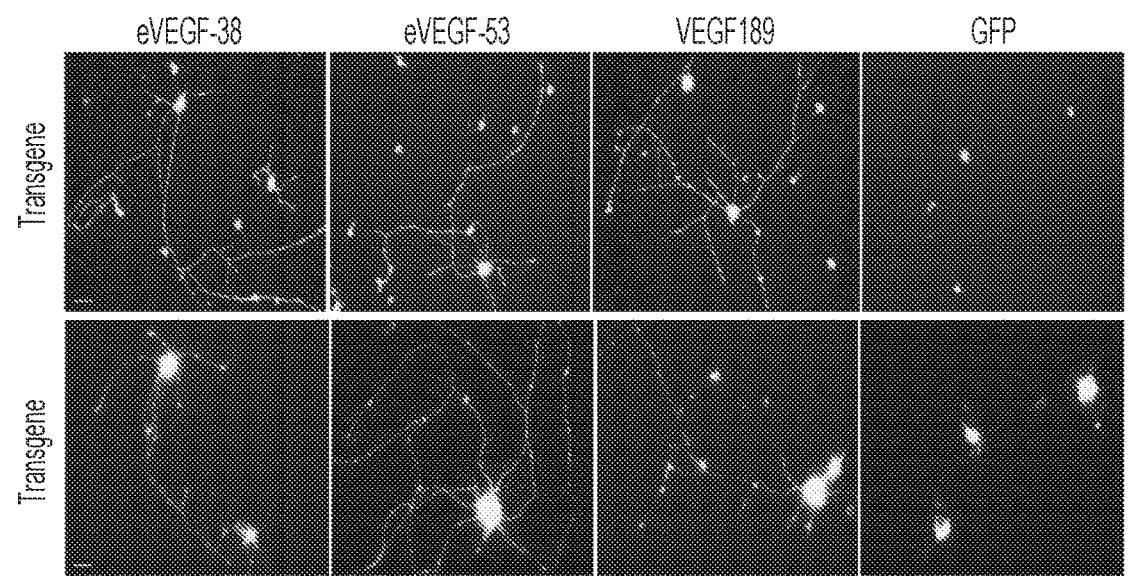
FIG. 5B is a series of photomicrographs of representative images for long axons formation induced by engineered VEGF's and VEGF189, bar=10 μm.
Figure 5C:
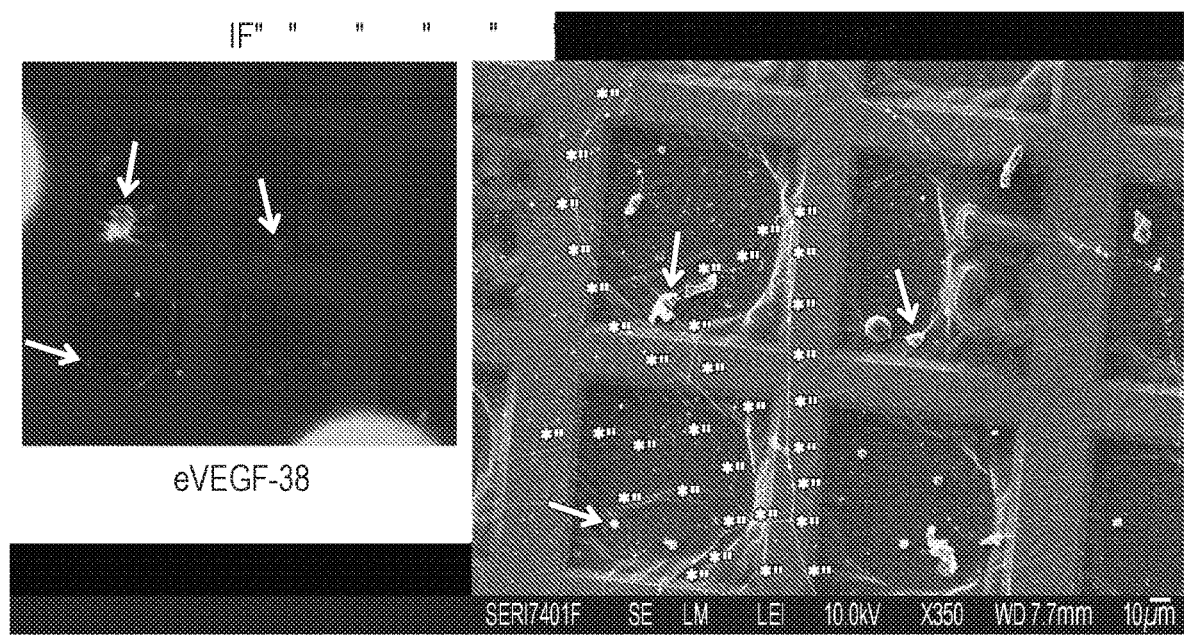
FIG. 5C is a series of photomicrographs showing correlative fluorescence and electron microscopy showing eVEGF-38 overexpressing RGC (green in IF) forming long axons as detected by SEM, whereas untransduced RGC (blue arrows) do not form long axons. These figures demonstrate that overexpression of eVEGF-38, eVEGF-53, and VEGF189 induces the growth and/or regeneration of long axons by the primary mouse RGC compared to the GFP control.
Figure 6:
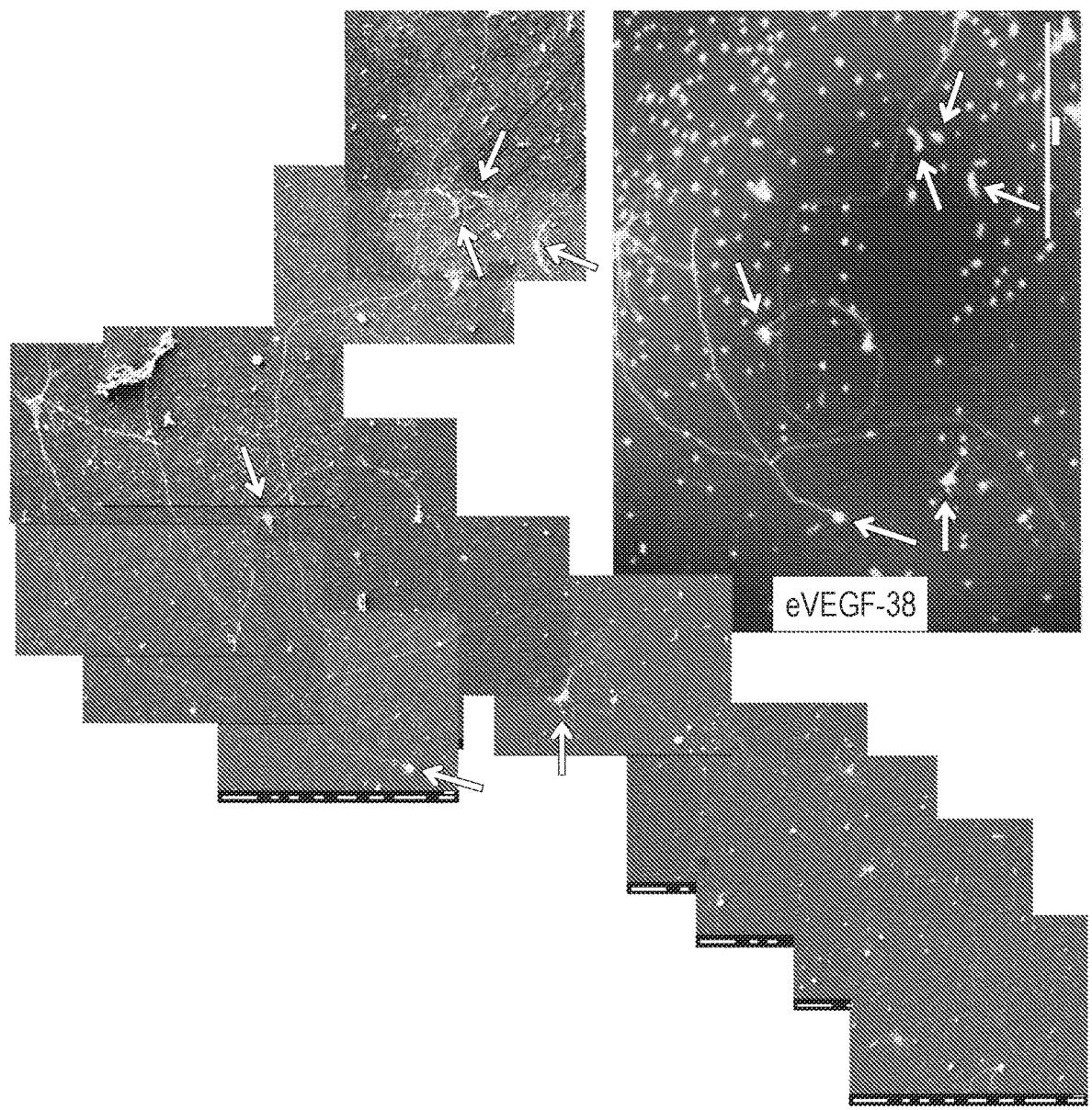
FIG. 6 is a series of photomicrographs showing correlative fluorescence and electron microscopy showing extra long axons (>1400 μm) from some of the eVEGF-38 overexpressing primary RGC. Green arrows, eVEGF-38 overexpressing cells; blue arrows, untransduced primary mouse RGC.
Figure 7A:
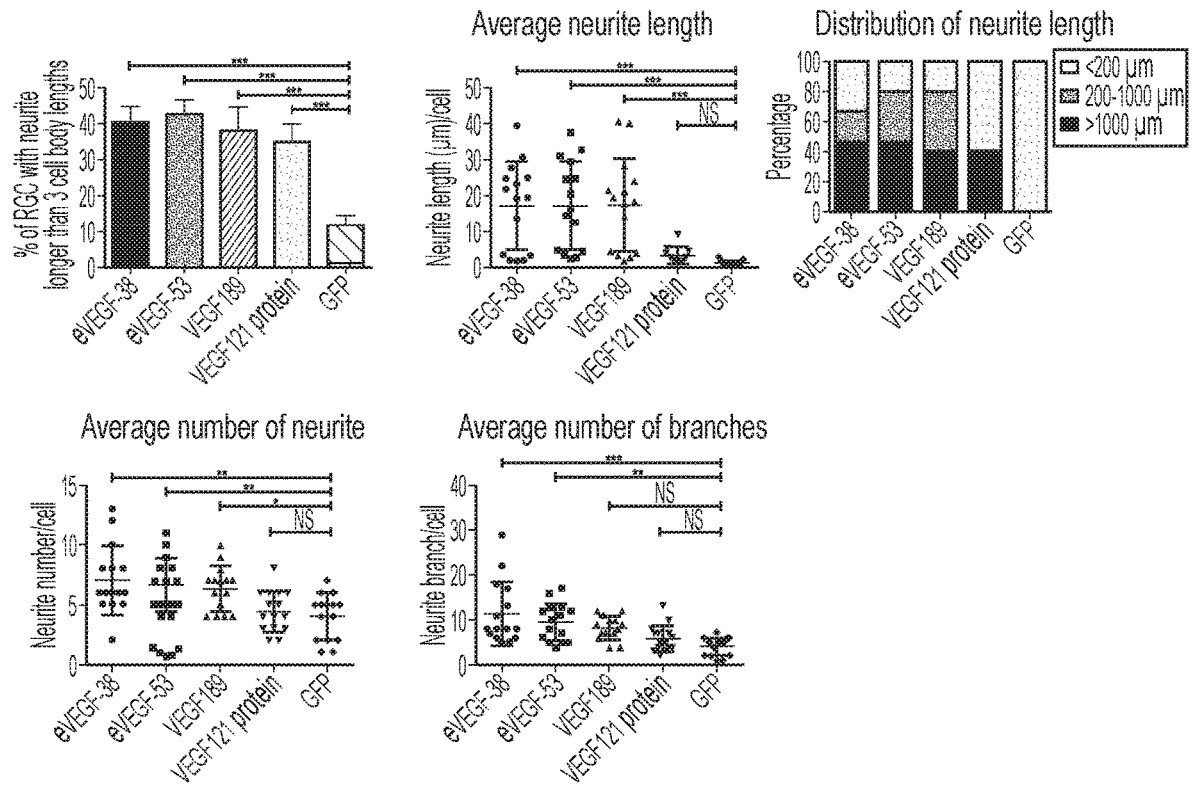
FIGS. 7A and 7B are a series of bar graphs and dot plots showing that VEGFR2 signaling is required for the formation of long axons by primary RGC overexpressing eVEGF-38, eVEGF-53, and VEGF189.
Figure 7B:
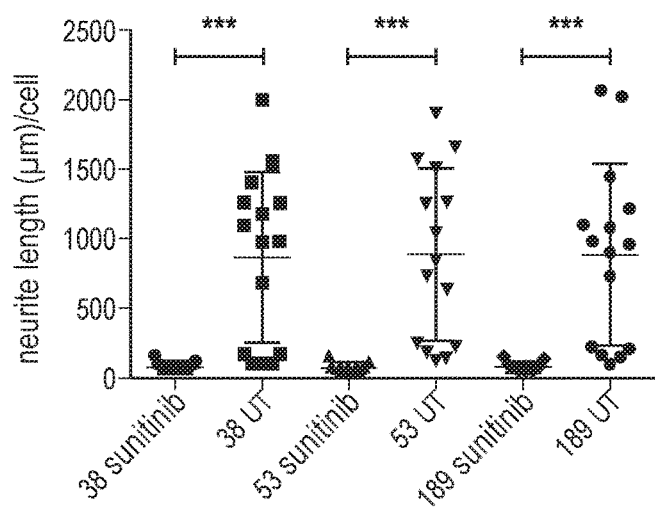
Figure 8:
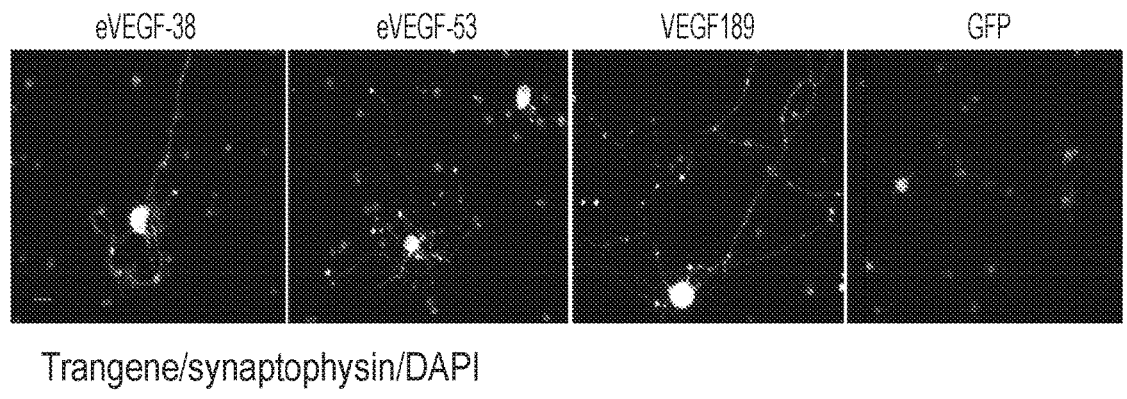
FIG. 8 is a series of photomicrographs showing that the axons and neurites from primary RGC overexpressing eVEGF-38, eVEGF-53, and VEGF189 also express synaptic vesicle marker synaptophysin. Bar=10 μm.
Figure 9:
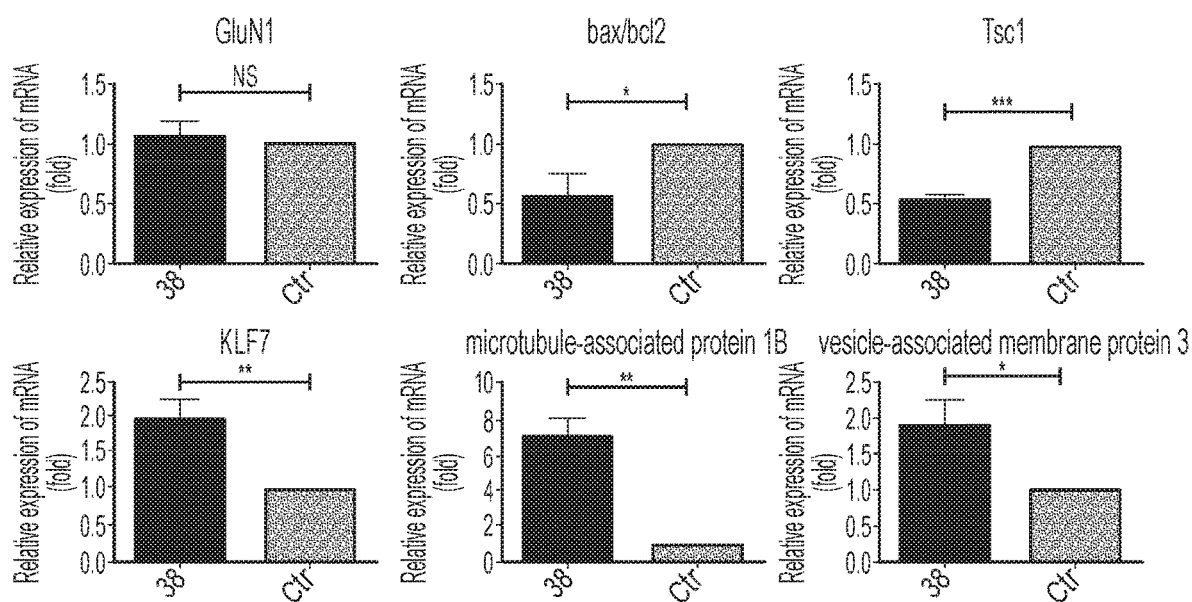
FIG. 9 is a series of bar graphs showing that overexpression of eVEGF-38 in primary RGC suppresses genes that are associated with cell death and suppression of axon formation, but induces genes that are associated with axon growth and neuronal function. Label: 38, eVEGF-38; Ctr, GFP control. Data=mean±SD, n=3 independent wells of primary RGC, *P<0.05, P<0.01, *P<0.001 by unpaired t-test.

The data showed that the novel engineered VEGF chimeric polypeptides eVEGF-38 and eVEGF-53 were effective in activating VEGFR2 in a cell-autonomous fashion (FIGS. 2A-B), confirming that both eVEGF-38 and eVEGF-53 are functional and can activate the high affinity VEGFR2 as membrane-tethered engineered VEGF proteins. Both eVEGF-38 and eVEGF-53, packaged into adeno-associated virus serotype 2 (AAV2) for efficient delivery to various cell types including RGC, significantly protected transduced primary mouse RGC from apoptosis in culture as well as from $H_2O_2$-induced cell death mostly in an autonomous manner (i.e. mainly the RGC expressing engineered VEGF chimeric polypeptides are protected) and via the activation of PI3K/Akt pathway (FIGS. 3 and 4). Overexpression of the natural VEGF189 isoform also resulted in activation of VEGFR2 and protected primary mouse RGC in culture and against $H_2O_2$-induced cell death, suggesting that localized VEGF189 proteins can also promote RGC survival (FIGS. 3A-B and FIGS. 4A-B). Furthermore, eVEGF-38 and eVEGF-53 chimeric polypeptides and VEGF189 expression enhanced axons and neurites formation of primary mouse RGCs (FIGS. 5A-C, FIG. 6, and FIGS. 7A-B), supported synaptogenesis and likely neuronal function (FIG. 8), which are consistent with the role of VEGF in promoting neurogenesis and neuronal function in vitro and in vivo. Gene expression analysis of eVEGF-38 overexpressing primary mouse RGC resulted in the down-regulation of genes involved in apoptosis and cell death (bax/bcl2 ratio) and inhibition of axon formation (Tsc1), but the up-regulation of genes involving in axon growth in neurons (Krüppel-like transcription factor 7, KLF7), neurogenesis (Microtubule-associated protein 1B), and synaptic vesicle trafficking (vesicle-associated membrane protein 3) (FIG. 9), suggesting that overexpression of eVEGF-38 chimeric polypeptide in RGC can promote neuronal survival, axon regeneration and neuronal function. Together, the data support overexpression of eVEGF-38, eVEGF-53 and the natural VEGF189 isoform in RGC promotes cell-autonomous RGC survival, axon growth and regeneration, and neuronal function, and is useful and a therapeutic agent for treatment of glaucoma. The chimeric polypeptides can be used therapeutically via a gene therapy approach (AAV) for eVEGF-38, eVEGF-53 and VEGF189. Activity is tested in animal models of glaucoma and optic nerve injury/regeneration.

Transmembrane Anchors

There are mainly three classes of membrane anchor/attachment that were considered for the engineered VEGF-A dimer (or concatemer):
1) Glycophosphatidylinositol (GPI) anchor (lipid anchor), and with a flexible peptide linker to connect with the functional protein.
2) Protein with a strong binding domain for extracellular matrix, such as a strong heparin-binding domain (e.g. VEGF189 protein).
3) Transmembrane (TM) anchor, both type I and type II which can be based on various naturally occurring transmembrane proteins such as cell surface receptors (e.g. PDGFRs, Neuropilins, VEGFRs, etc) and transmembrane protein ligands (e.g. Delta 4, Jagged), and with a flexible peptide linker to connect with the functional protein.

Alternatives can also be used, e.g., as described herein and Choi et al., 2013, Physiology 28:164-171, the entire contents of which is hereby incorporated by reference. These three classes of membrane anchor/attachment are preferred at this time for tethering a polypeptide (VEGF) to the membrane and making the functional polypeptide to face the outside compartment of the cell (extracellular). A flexible linker is favored for allowing the membrane tethered proteins to be functional (outside the cell), meaning the amino acids composition as well as the length of the flexible peptide linker can affect the activity of the resulting membrane tethered proteins especially how it can bind to and activate its receptors on the cell surface. For the GPI-anchor eVEGF constructs described herein, a flexible linker that has 38 amino acids and a longer one with 53 amino acids was used. Linkers with lengths of 39-52 amino acids are also useful. Flexible linkers ranging in size from 10-100 amino acids are also useful, e.g., 25-85 amino acids, 30-60, inclusive amino acids, and for example, between 38 and 53 amino acids inclusive lengths.

Other lipid anchors such as by prenylation, and fatty acylated protein (via N-myristoylation and S-palmitoylation) may also be used to tethered the protein to the cell membrane, however, these approaches are used for intracellular proteins and are tailored for proteins that are designed to function outside the cell and in the extracellular side of membrane vesicles (such as VEGF-A).

FIGS. 10A, 10B, and 10C show the sequence and constructs of eVEGF-38, e-VEGF-53, and VEGF189. The figures show detailed AA sequences for the GPI anchor, strong heparin binding domain, examples of TM anchors, as well as the complete aa sequences of eVEGF-38, eVEGF-53, and VEGF189.

Examples of transmembrane (TM) anchors are described below.

```
PDGF receptor beta TM domain:
                              (SEQ ID NO: 4)
N'-VVISAILALVVLTIISLIILI-C'.
```

In this case, the VEGF dimer will be attached to the N-terminus of the transmembrane domain with a flexible linker (SEQ ID NO: 5):

```
SP (SEQ ID NO: 12)-VEGF (SEQ ID NO: 13)-linker (SEQ ID NO: 14; 20 amino acid)-VEGF(SEQ ID NO: 13)- linker (SEQ ID NO: 15 or 17; 38 to 53 amino acid)-

VVISAILALVVLTIISLIILI (SEQ ID NO: 4).
```

```
Neuropilin-1 TM anchor:
                              (SEQ ID NO: 6)
N'-ILITIIAMSALGVLLGAVCGVVL-C'.
```

In this case, the VEGF dimer will be attached to the N-terminus of the transmembrane domain with a flexible linker (SEQ ID NO: 7):

```
SP (SEQ ID NO: 12)-VEGF (SEQ ID NO: 13)-linker (SEQ ID NO: 14; 20 amino acid)-VEGF(SEQ ID NO: 13)- linker (SEQ ID NO: 15 or 17; 38 to 53 amino acid)-

ILITIIAMSALGVLLGAVCGVVL (SEQ ID NO: 6).
```

```
VEGFR2 TM anchor:
                              (SEQ ID NO: 8)
N'-IIILVGTAVIAMFFWLLLVII-C'.
```

In this case, the VEGF dimer will be attached to the N-terminus of the transmembrane domain with a flexible linker (SEQ ID NO: 9):

```
SP (SEQ ID NO: 12)-VEGF (SEQ ID NO: 13)-linker (SEQ ID NO: 14; 20 amino acid)-VEGF(SEQ ID NO: 13)- linker (SEQ ID NO: 15 or 17; 38 to 53 amino acid)-

IIILVGTAVIAMFFWLLLVII (SEQ ID NO: 8).
```

```
Delta-like-4 (Dl4) transmembrane anchor:
                                   (SEQ ID NO: 10)
N'-VAVSLGVGLAVLLVLLGMVAV-C'.
```

In this case, the VEGF dimer will be attached to the N-terminus of the transmembrane domain with a flexible linker (SEQ ID NO: 11):

```
SP (SEQ ID NO: 12)-VEGF (SEQ ID NO: 13)-linker (SEQ ID NO: 14; 20 amino acid)-VEGF(SEQ ID NO: 13)- linker (SEQ ID NO: 15 or 17; 38 to 53 amino acid)-

VAVSLGVGLAVLLVLLGMVAV (SEQ ID NO: 10).
```

General considerations about where the membrane anchor is attached is further described below. For GPI anchor, it should be attached to the C-terminal of the engineered VEGF for correct processing of the GPI anchor without disrupting the signal peptide of the engineered protein. For the strong heparin-binding domain (for example in VEGF189), it can be inserted anywhere in the engineered VEGF protein as long as such insertion does not interfere with receptors binding (function) and the secretion of the resulting VEGF outside the cell. For type I transmembrane anchor (see examples above), it should be attached to the C-terminal of the engineered VEGF so that the VEGF is targeted to the ER lumen (facing the extracellular space) after final protein synthesis and processing in the ER and Golgi. For type II TM anchor, it should be attached the N-terminal of the engineered VEGF so that the VEGF is targeted to the ER lumen (facing the extracellular space after final protein processing.

Engineered VEGF Chimeric Polypeptides for Glaucoma

The constructs described herein are used to reduce and/or prevent RGC degeneration in glaucoma. Accordingly, the eVEGF constructs promote RGC survival and/or provide neuroprotection of the RGC in pathologies involving RGC cell death, such as glaucoma. The therapy prevents and/or inhibits neurodegeneration and induces axon growth/regeneration for neurons including retinal ganglion cell in the retina, thus providing a clinical benefit to individuals diagnosed as suffering from retinal neuro-degenerative disease such as glaucoma. Currently, there is no similar therapeutic approach that involves using engineered VEGF chimeric polypeptides for neuroprotection and to induce axon growth for retinal neuro-degenerative diseases, particularly with the advantage of minimizing or eliminating effects on bystander cells.

Previous neuroprotection approaches for retinal neurodegenerative diseases have not performed well in the clinical setting; the compositions described herein overcome the drawbacks of earlier approaches and have the added advantage of few adverse side effects due to the minimization of bystander cell effects. The engineered VEGF chimeric polypeptides and VEGF189 overcome many of the limitations of the other neuroprotective molecules and the data indicates that the engineered VEGF chimeric polypeptides are superior neuroprotectant for retinal neurons. However, one cannot use VEGF directly in the eye because of its potent effect on inducing angiogenesis, vascular permeability and vascular inflammation (leukostasis), which can cause severe retinal pathologies. The design of the engineered chimeric polypeptides described herein and also VEGF189 overcomes this negative effect of natural secreted and diffusible VEGFs, by tethering the eVEGF-38 and eVEGF-53 to the cell membrane and by taking advantage of the strong HSPG binding nature of VEGF189 isoform that their effects will be limited to the cells that are expressing them in an autocrine fashion (FIG. 1A-B). The engineered VEGF chimeric polypeptides and VEGF189 have the added benefit of promoting neurite growth and neuronal function in the retinal neurons overexpressing them, in addition to protecting the neuronal from dying.

Modified Proteins or Peptides

Hybrid proteins comprising a polypeptide or fragment thereof may be linked to other types of polypeptides. These additional polypeptides may be any amino acid sequence useful for the purification, identification, overall charge of the protein or peptide, and/or therapeutic or prophylactic application of the peptide. In addition, the additional polypeptide can be a signal peptide, or targeting peptide, etc. The terms "peptide," "polypeptide," and "protein" are used interchangeably herein, although typically they refer to peptide sequences of varying sizes. It may be referred herein, to the amino acid-based compositions of the invention as "polypeptides" to convey that they are linear polymers of amino acid residues, and to help distinguish them from full-length proteins. A polypeptide of the invention can "constitute" or "include" a fragment of a VEGF polypeptide, and the invention encompasses polypeptides that constitute or include biologically active variants of VEGF.

In some cases, the VEGF polypeptide can include additions, substitutions or deletions may increase the stability (including but not limited to, resistance to proteolytic degradation) of the polypeptide or increase affinity of the polypeptide for its binding proteins. In some cases, the additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport through tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which do not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to agonists, super-agonists, partial agonists, inverse agonists, antagonists, receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. For example, locations in the polypeptide required for biological activity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

The bonds between the amino acid residues can be conventional peptide bonds or another covalent bond (such as an ester or ether bond), and the polypeptides can be modified by amidation, phosphorylation or glycosylation. A modification can affect the polypeptide backbone and/or one or more side chains. Chemical modifications can be naturally occurring modifications made in vivo following translation of an mRNA encoding the polypeptide (e.g., glycosylation in a bacterial host) or synthetic modifications made in vitro. A biologically active variant of a VEGF polypeptide can include one or more structural modifications resulting from any combination of naturally occurring (i.e., made naturally in vivo) and synthetic modifications (i.e., naturally occurring or non-naturally occurring modifications made in vitro). Examples of modifications include, but are not limited to, amidation (e.g., replacement of the free carboxyl group at the C-terminus by an amino group); biotinylation (e.g., acylation of lysine or other reactive amino acid residues with a biotin molecule); glycosylation (e.g., addition of a glycosyl group to either asparagines, hydroxylysine, serine or threonine residues to generate a glycoprotein or glycopeptide); acetylation (e.g., the addition of an acetyl group, typically at the N-terminus of a polypeptide); alkylation (e.g., the addition of an alkyl group); isoprenylation (e.g., the addition of an isoprenoid group); lipoylation (e.g. attachment of a lipoate moiety); and phosphorylation (e.g., addition of a phosphate group to serine, tyrosine, threonine or histidine).

As discussed above, one or more of the amino acid residues in a biologically active variant may be a non-naturally occurring amino acid residue. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine(2R,3S)-2-amino-3-methylpentanoic acid and L-cyclopentyl glycine (S)-2-amino-2-cyclopentyl acetic acid. For other examples, one can consult textbooks or the worldwide web (a site is currently maintained by the California Institute of Technology and displays structures of non-natural amino acids that have been successfully incorporated into functional proteins).

Alternatively, or in addition, one or more of the amino acid residues in a biologically active variant can be a naturally occurring residue that differs from the naturally occurring residue found in the corresponding position in a wildtype sequence. In other words, biologically active variants can include one or more amino acid substitutions. We may refer to a substitution, addition, or deletion of amino acid residues as a mutation of the wildtype sequence. As noted, the substitution can replace a naturally occurring amino acid residue with a non-naturally occurring residue or just a different naturally occurring residue. Further the substitution can constitute a conservative or non-conservative substitution. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The polypeptides that are biologically active variants of a VEGF polypeptide can be characterized in terms of the extent to which their sequence is similar to or identical to the corresponding wild-type polypeptide. For example, the sequence of a biologically active variant can be at least or about 80% identical to corresponding residues in the wild-type polypeptide. For example, a biologically active variant of a VEGF polypeptide can have an amino acid sequence with at least or about 60% sequence identity (e.g., at least or about 65%, 70%, 80%, 85%, 90%, 95%, 97%, 98%, or 99% sequence identity) to a VEGF polypeptide or to a homolog or ortholog thereof.

The biological activity can be assessed in ways known to one of ordinary skill in the art and includes, without limitation, in vitro cleavage assays or functional assays.

Expression Vectors

Delivery vehicles as used herein, include any types of molecules for delivery of the compositions embodied herein, both for in vitro or in vivo delivery. Examples, include, without limitation: expression vectors, nanoparticles, colloidal compositions, lipids, liposomes, nanosomes, carbohydrates, organic or inorganic compositions and the like.

In some embodiments, a delivery vehicle is an expression vector, wherein the expression vector comprises an isolated nucleic acid sequence encoding a VEGF chimeric polypeptide embodied herein.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. A wide variety of host/expression vector combinations may be used to express the nucleic acid sequences described herein. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described.

Useful vectors include, for example, viral vectors (such as adenoviruses ("Ad"), adeno-associated viruses (AAV), lentiviruses, and vesicular stomatitis virus (VSV) and retroviruses). Replication-defective recombinant adenoviral vectors, can also be used. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; *BioTechniques*, 34: 167-171 (2003).

In one embodiment, the viral vector is an adenovirus vector, an adeno-associated viral vector (AAV), or derivatives thereof. The adeno-associated viral vector comprises AAV serotypes 1, 2, 3, 4, 5, 6, 7, 8, 9, 10, 11, DJ or DJ/8. In one embodiment, the AAV vector is AAV serotype 2. (AAV2).

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Viral vectors can include a strong eukaryotic promoter operably linked to the polynucleotide e.g., a cytomegalovirus (CMV) promoter. The recombinant viral vector can include one or more of the polynucleotides therein, preferably about one polynucleotide. In some embodiments, the viral vector used in the invention methods has a pfu (plague forming units) of from about $10^8$ to about $5 \times 10^{10}$ pfu. In embodiments in which the polynucleotide is to be administered with a non-viral vector, use of between from about 0.1 nanograms to about 4000 micrograms will often be useful e.g., about 1 nanogram to about 100 micrograms.

Additional vectors include retroviral vectors such as Moloney murine leukemia viruses and HIV-based viruses. One HIV-based viral vector comprises at least two vectors wherein the gag and pol genes are from an HIV genome and the env gene is from another virus. DNA viral vectors include pox vectors such as orthopox or avipox vectors, herpesvirus vectors such as a herpes simplex I virus (HSV) vector.

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated virus, in some embodiments, may exhibit much longer expression. The particular vector chosen will depend upon the target cell and the condition being treated. The selection of appropriate promoters can readily be accomplished. An example of a suitable promoter is the 763-base-pair cytomegalovirus (CMV) promoter. Other suitable promoters which may be used for gene expression include, but are not limited to, the Rous sarcoma virus (RSV), the SV40 early promoter region, the herpes thymidine kinase promoter, the regulatory sequences of the metallothionein (MMT) gene, prokaryotic expression vectors such as the β-lactamase promoter, the tac promoter, promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells, insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in myeloid cells, myelin basic protein gene control region which is active in oligodendrocyte cells in the brain, myosin light chain-2 gene control region which is active in skeletal muscle, and gonadotropic releasing hormone gene control region which is active in the hypothalamus. Certain proteins can expressed using their native promoter. Other elements that can enhance expression can also be included such as an enhancer or a system that results in high levels of expression such as a taat gene and tar element. This cassette can then be inserted into a vector, e.g., a plasmid vector such as, pUC19, pUC118, pBR322, or other known plasmid vectors, that includes, for example, an *E. coli* origin of replication. The plasmid vector may also include a selectable marker such as the 0-lactamase gene for ampicillin resistance, provided that the marker polypeptide does not adversely affect the metabolism of the organism being treated. The cassette can also be bound to a nucleic acid binding moiety in a synthetic delivery system.

The nucleic acids and polypeptides described herein may be referred to as "exogenous". The term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

Recombinant constructs are also provided herein and can be used to transform cells in order to express the VEGF chimeric polypeptides. A recombinant nucleic acid construct comprises a nucleic acid encoding, for example SEQ ID NOS: 1, 2 or 3, is operably linked to a regulatory region suitable for expressing the VEGF chimeric polypeptides in the particular cell. It will be appreciated that a number of nucleic acids can encode a polypeptide having a particular amino acid sequence. The degeneracy of the genetic code is well known in the art. For many amino acids, there is more than one nucleotide triplet that serves as the codon for the amino acid. For example, codons in the coding sequence for VEGF can be modified such that optimal expression in a particular organism is obtained, using appropriate codon bias tables for that organism.

Disorders

Ocular disorders that can be treated using a method of the present disclosure include, but are not limited to, macular degeneration, choroidal neovascularization, macular edema, retinal neovascularization, proliferative vitreoretinopathy, glaucoma, and ocular inflammation.

Ocular diseases that can be treated using a method of the present disclosure include, but are not limited to, acute macular neuroretinopathy; Behcet's disease; choroidal neovascularization; diabetic uveitis; histoplasmosis; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy and diabetic macular edema), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; non-retinopathy diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber's hereditary optic neuropathy; retinopathy of prematurity; and disorders of color vision, including achromatopsia, protanopia, deuteranopia, and tritanopia.

In some cases, the ocular disease is glaucoma, retinitis pigmentosa, macular degeneration, retinoschisis, Leber's Congenital Amaurosis, diabetic retinopathy, achromotopsia, or color blindness.

Embodiments of the invention are also directed to treatment of any disease or disorder wherein VEGF is protective such as neurodegenerative diseases, e.g. Niemann-Pick disease, Alzheimer's disease, Parkinson's disease, Lou Gehrig's disease, schizophrenia, Gaucher disease, Fabry disease, Tay-Sachs disease, Sandhoff disease and cerebellar ataxia, but is not limited thereto.

Pharmaceutical Compositions

As described above, the compositions of the present invention can be prepared in a variety of ways known to one of ordinary skill in the art. Regardless of their original source or the manner in which they are obtained, the compositions of the invention can be formulated in accordance with their use. For example, the nucleic acids and vectors described above can be formulated within compositions for application to cells in tissue culture or for administration to a patient or subject. Any of the pharmaceutical compositions of the invention can be formulated for use in the preparation of a medicament, and particular uses are indicated below in the context of treatment. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intra-arterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, polypeptides, nucleic acids and vectors described herein in combination with one or more pharmaceutically acceptable carriers. The term pharmaceutically acceptable carrier, includes any and all solvents, dispersion media, coatings, antibacterial, isotonic and absorption delaying agents, buffers, excipients, binders, lubricants, gels, surfactants and the like, that may be used as media for a pharmaceutically acceptable substance. In making the compositions of the invention, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), lotions, creams, ointments, gels, soft and hard gelatin capsules, suppositories, sterile injectable solutions, and sterile packaged powders. As is known in the art, the type of diluent can vary depending upon the intended route of administration. The resulting compositions can include additional agents, such as preservatives. In some embodiments, the carrier can be, or can include, a lipid-based or polymer-based colloid. In some embodiments, the carrier material can be a colloid formulated as a liposome, a hydrogel, a microparticle, a nanoparticle, or a block copolymer micelle. As noted, the carrier material can form a capsule, and that material may be a polymer-based colloid.

In some instances, the topical ocular formulation is a solution, a suspension, creams, ointments, gels, gel-forming liquid, suspension containing liposomes or micelles, spray formulation, or an emulsion. In some cases, the topical ocular formulation also includes one or more pharmaceutically acceptable excipients selected from stabilizers, surfactants, polymer base carriers, gelling agents, organic co-solvents, pH active components, osmotic active components and with or without preservatives. In some cases, the sustained release semi-solid formulation, sustained release solid formulation or ocular implant is injected into the affected eye. In some embodiments, the sustained release semi-solid formulation, sustained release solid formulation or ocular implant further comprises a pharmaceutically acceptable excipient. In some cases, the sustained release semi-solid formulation, sustained release solid formulation or ocular implant includes a eVEGF-38, eVEGF-53, VEGF189 or combinations thereof; and a biodegradable polymer selected from polylactic acid (PLA), polyglycolic acid (PLGA) and polylactic acid and polyglycolic acid copolymers.

The ophthalmic formulations further comprise at least one ophthalmically acceptable excipient such as, but not limited to, demulcent, tonicity adjusting agent, preservative, buffering agent, pH adjusting agent, solubilizing agent, surfactant, chelating agent, penetration enhancer, emulsifying agent, suspending agent, stabilizing agent, antioxidant, carrier, plasticizer, release modifying or controlling excipients, ion exchange resins and the like. Suitable demulcents include, but are not limited to, glycerin, polyvinyl pyrrolidone, polyethylene oxide, polyethylene glycol (PEG) such as but not limited to PEG 400, PEG 300 and the like or combinations thereof; propylene glycol, sorbitol and polyacrylic acid and the like or combinations thereof. Tonicity adjusting agents useful in the compositions of the present invention may include, but are not limited to, salts such as, but not limited to, sodium chloride, potassium chloride and calcium chloride, non-ionic tonicity agents may include, but are not limited to, propylene glycol, glycerol, mannitol, dextran and the like or combinations thereof.

Suitable chelating agents may include, but are not limited to, EDTA and its salts. Solubilizing agents, that may be employed include, but are not limited to, CREMOPHOR EL®, tween 80, cyclodextrin and the like or combinations thereof. Suitable cyclodextrins may be employed, such as, but not limited to, α-cyclodextrin, β-cyclodextrin γ-cyclodextrin, hydroxypropyl-β-cyclodextrin, hydroxypropyl-γ-cyclodextrin, dimethyl-β-cyclodextrin and dimethyl-γ-cyclodextrin, and the like or combinations thereof. pH adjusting agents may include sodium hydroxide, hydrochloric acid, boric acid, Tris, triethanolamine and sodium hydroxide. Suitable buffering agents include, but are not limited to, phosphates, acetates and the like, and amino alcohols such as 2-amino-2-methyl-1-propanol (AMP), ascorbates, borates, hydrogen carbonate/carbonates, citrates, gluconates, lactates, propionates and TRIS (tromethamine) buffers, and the like or combinations thereof. Suitable preservatives include, but are not limited to, benzalkonium chloride, polyquatemium-1, p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, sorbic acid, and the like or combinations thereof. Suitable penetration enhancers that may optionally be employed include, but are not limited to, polyoxyethylene glycol lauryl ether, polyoxyethylene glycol stearyl ether, polyoxyethylene glycol oleyl ether, sodium taurocholate, saponins, CREMOPHOR EL, and the like or combinations thereof.

Suitable surfactants that may be employed include, but are not limited to, ionic and nonionic surfactants, and the like or combinations thereof. Suitable nonionic surfactants include, but are not limited to, poloxamers, tyloxapol, polysorbates, polyoxyethylene castor oil derivatives, sorbitan esters, polyoxyl stearates and a mixture of two or more thereof. Suitable pharmaceutical carriers include sterile water; electrolytes such as sodium chloride; dextrose; dextrose in water or saline; lower alkanols, ointment bases such as but not limited to, natural wax e.g. white bees wax, carnauba wax, wool wax (wool fat), purified lanolin, anhydrous lanolin; petroleum wax e.g. solid paraffin, microcrystalline wax; hydrocarbons e.g. liquid paraffin, white petrolatum (e.g. white PROTOPET®), yellow petrolatum, and the like or combinations thereof. Suitable emulsifying agent may be included such as, but not limited to, mono- or di-glyceride of a fatty acid, phosphatide, e.g., lecithin, polysorbates, macrogols, poloxamers, tyloxapol, polyethylene glycol derivatives, polyvinyl alcohol and the like, and mixtures thereof. Suitable stabilizing agent such as, but not limited to, polyethylene glycol hydroxystearate, thiourea, thiosorbitol, sodium dioctyl sulfosuccinate, monothioglycerol and the like, or combinations thereof may be employed. Antioxidants such as, but not limited to, ascorbic acid, acetylcysteine, cysteine, sodium hydrogen sulfite, butylated hydroxyanisole, butylated hydroxytoluene or alpha-tocopherol acetate may be employed. Plasticizers, such as, but not limited to, glycerol, and the like may be employed.

Release modifying or controlling excipients, such as but not limited to, polymeric release modifying or controlling excipients, non-polymeric release modifying or controlling excipients or combinations thereof may be included in the compositions of the present invention. Exemplary release modifying or controlling excipients include glyceryl behenate, chitosan, carrageenan, cellulose derivatives such as ethylcellulose, acrylic acid and methacrylic acid polymers or copolymers and the like, or derivatives or combinations thereof. The ophthalmic formulations of the present invention may optionally include additional viscosity enhancing agents such as, but not limited to, cellulose and cellulose derivatives, such as, but not limited to, methylcellulose, hydroxypropylcellulose, hydroxyethyl cellulose, ethylhydroxyethyl cellulose, hydroxypropylmethylcellulose, sodium carboxymethylcellulose, cellulose acetophthalate, and the like or combinations thereof; alginic acid, sodium alginate, propylene glycol alginate, polyvinylpyrrolidone, carboxyvinyl polymers or carbomers (CARBOPOL®), polyvinyl alcohol, glycerin, polyethylene glycol, triblock copolymers of polyoxypropylene and polyoxyethylene, polyethoxylated sorbitan, polysorbate 80, chondroitin sulfate, dimethicone, perfluorononyl dimethicone, cyclomethicone, dextrans, proteoglycans, natural polysaccharides, such as, but not limited to, hyaluronic acid and salts thereof, guar gum, karaya, xyloglucan gum, chitosan, gellan gum, pectin, collagen, modified collagen and like or combinations thereof.

The ophthalmic formulations of the present invention may optionally include additional gelling agents such as, but not limited to, polysaccharide gums such as, but not limited to, gellan gum, tamarind gum, tragacanth, locust bean gum, agarose, carageenans, guar gum, hydroxypropyl guar gum, hyaluronic acid, chitosan, konjac, acacia, pectin, arabic, curdlan, glucan gum, scleroglucan and sulfated glucan sulfate and the like or combinations thereof; cellulose and its derivatives such as, but not limited to, methyl cellulose, carboxymethyl cellulose, methyl cellulose, hydroxypropyl cellulose, methyl hydroxypropyl cellulose, hydroxypropyl methyl cellulose, cellulose acetate, ethyl cellulose, methyl hydroxyethyl cellulose, hydroxyethyl cellulose, cellulose gum, and the like or combinations thereof; cross-linked acrylic polymers or carbomer (CARBOPOL™), aloe vera gel, polyvinyl alcohol, polyacrylamide, poloxamer, polymethylvinylether-maleic anhydride, swellable water-insoluble polymers such as, but not limited to, hydrogel and the like or combinations thereof. Ion exchange resins such as, but not limited to, inorganic zeolites or synthetically produced organic resins may be employed in the compositions of the present invention. The ophthalmic formulations of the present invention may optionally include additional mucodhesive agents such as, but not limited to, polyacrylic acid, hyaluronans, chitosan, pullulan, cellulose derivatives such as, but not limited to, methyl cellulose, hydroxypropyl methyl cellulose, sodium carboxymethylcellulose, poly (galacturonic) acid, sodium alginate, pectin, xyloglucan, xanthan gum, carbomers (CARBOPOL™), polyvinyl alcohol, polyvinylpyrrolidone, polyethylene glycol, poloxamer, and the like or combinations thereof.

The above listing of examples is given for illustrative purposes and is not intended to be exhaustive. Examples of other agents useful for the foregoing purposes are well known in ophthalmic formulation and are contemplated by the present invention. It is also contemplated that the concentrations of the excipients in the formulations of the present invention can vary. The ophthalmic formulations of the present invention can be in the form of eye drops, eye lotions, suspensions, dispersions, gels, ointments, emulsions, colloidal solutions, ocular inserts, ocular hydrogels, films, minitablets, nanoemulsions, and particulate systems such as but not limited to, liposomes, microparticles, nanoparticles, and the like. In one embodiment, the ophthalmic formulation of the present invention is in the form of an in-situ gelling system. In another embodiment, the in-situ type gelling composition of the present invention may comprise one or more cross-linking agent, such as but not limited to borate, and the like. In another embodiment, the in-situ type gelling composition of the present invention does not comprise one or more cross-linking agent.

In a further embodiment, the ophthalmic formulation of the present invention in the form of ocular insert is a bioerodible ocular insert. In another embodiment, the ophthalmic formulation of the present invention in the form of ocular insert is a non-bioerodible ocular insert.

The ophthalmic formulations of the present invention may be in the form of liquid, solid or semisolid dosage form. Further, in one embodiment, the ophthalmic formulations of the present invention are formulated so as to have a pH and osmolality that are compatible with the eye. The ophthalmic formulations of the present invention may comprise depending on the final dosage form suitable ophthalmically acceptable excipients. In one embodiment, the ophthalmic formulations are formulated to maintain a physiologically tolerable pH range. In one embodiment, the pH range of the ophthalmic formulation is in the range of from 5 to 9. In another embodiment, pH range of the ophthalmic formulation is in the range of from 6 to 8.

In a further embodiment, the ophthalmic formulations of the present invention are for topical administration to the eye. In another embodiment, the ophthalmic formulations of the present invention are for intraocular or periocular administration. In a further embodiment, the ophthalmic formulations of the present invention are for immediate release of active agent in the ocular cavity.

In another embodiment, the ophthalmic formulations of the present invention are for sustained or controlled release in the ocular cavity. In a further embodiment, the ophthalmic formulations of the present invention are for at once-a-day administration. In one embodiment, the sustained or controlled release delivery of the active agent from the ophthalmic formulation is for a sustained period of time of about 24 hours. In another embodiment, the sustained or controlled release delivery of the active agent from the ophthalmic formulation is for a sustained period of time of about 12 hours. In a further embodiment, the sustained or controlled release delivery of the active agent from the ophthalmic formulation is for a sustained period of time of about 10 hours. In yet another embodiment, the sustained or controlled release delivery of the active agent from the ophthalmic formulation is for a sustained period of time of about 8 hours. In one embodiment, the sustained or controlled release delivery of the active agent from the ophthalmic formulation is for a sustained period of time of about 6 hours. In a further embodiment, the sustained or controlled release delivery of the active agent from the ophthalmic formulation is for a sustained period of time of about 4 hours to about 24 hours.

Depending on the dosage form of the ophthalmic formulations of the present invention, appropriate method of preparation is employed. Various methods for preparation of ophthalmic formulations known in the art may be employed. Further depending on the dosage form, the ophthalmic formulations or excipients and/or active agents employed therein are suitably sterilized by one or more methods known to a person skilled in the art. In one embodiment, the ophthalmic formulations of the present invention in the form of ocular insert, is prepared by molding or extrusion procedures well known in the art. In another embodiment, the ophthalmic formulation of the present invention in the form of ophthalmic solution is prepared by either by dissolving or suspending prescribed amount of a drug in a prescribed volume of a carrier solvent along ophthalmically acceptable excipients. Particle size of certain ophthalmic formulations of the present invention is within ophthalmically acceptable limits known to a person skilled in the art.

The compositions of the present invention are useful for the treatment of humans or animals.

VEGF Chimeric Polypeptides (eVEGF)

Vascular endothelial growth factor (VEGF) 121 isoform has potent retinal neuroprotective effects without promoting retinal inflammation. Two exemplary VEGF121 chimeric polypeptides (eVEGF) were made. These chimeric polypeptides promote cell autologous signaling via VEGFR2 and tested their neuroprotective function in vitro using primary mouse retinal ganglion cells (RGC).

eVEGF-38 and eVEGF-53 localize to the cell membrane and comprise myc-tags. VEGF189 was constructed with a myc-tag. The constructs were packaged into adeno-associated virus serotype 2 (AAV2) for efficient transduction and expression in human microvascular endothelial cells (hREC) and RGC. Transgenes expression was measured by western blot, qPCR and immunostaining. In hREC, VEGFR2, VCAM-1, E-selectin and tissue factor expression were measured by immunostaining or qPCR. VEGFR2 signaling, axon length, and synapse formation in RGC were measured by immunostaining. RGC survival was measured by TUNEL staining and intracellular $[Ca_{2+}]$ was measured using fura2/AM calcium imaging.

In hREC, eVEGF-38 and eVEGF-53 expression was detected in cell lysate but not in conditioned media. Increased VEGFR2 phosphorylation and expression was detected at the cell membrane. Pro-inflammatory markers were increased by VEGF189/AAV2 and VEGF165 protein (p<0.05), but not by eVEGF-38/AAV2 or eVEGF-53/AAV2 compared with GFP/AAV2 control. In RGC, high expression levels of all transgenes as well as phosphor-ERK and phospho-AKT were detected, and average lengths of RGC axons were increased by 500% (p<0.001) compared to control, while VEGFR2 inhibition completely blocked axon development in the RGC. Both eVEGFs/AAV2 and VEGF189/AAV2 promoted synapse formation in RGC. eVEGF-38/AAV2, eVEGF-53/AAV2, VEGF189/AAV2, and exogenous VEGF121 protein promoted RGC survival compared to control (45%, 48%, 50%, 62% vs. 22% survival, P<0.001). Expression of eVEGF-38, eVEGF-53, and VEGF189 significantly enhanced RGC survival upon $H_2O_2$ treatment (10%, 15%, 18% increased survival compared to control, P<0.05), which was abolished by LY-294002 treatment. Lastly, eVEGF-38 and eVEGF-53 expression decreased intracellular [Ca2+] upon carbachol and NMDA stimulation compared to control.

The engineered VEGF chimeric polypeptides significantly promoted RGC axon formation, survival as well as synapse formation, and represent useful therapeutics for retinal neuroprotection for glaucoma.

Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. In some embodiments, a sufficient number of weaker interactions can provide sufficient stability for moieties to remain physically associated under a variety of different conditions.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. A "nucleotide sequence encoding" an amino acid sequence includes all nucleotide sequences that are degenerate versions of each other and that encode the same amino acid sequence.

"Excipient" is used herein to include any other compound that may be contained in or combined with one or more of the disclosed recombinant VEGF molecules that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients. For the purposes of the present application the term "excipient" and "carrier" are used interchangeably throughout the description of the present application and said terms are defined herein as, "ingredients which are used in the practice of formulating a safe and effective pharmaceutical composition."

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified protein or peptide is free of amino acids/amino acid sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The term "signal peptide" or "signal peptide sequence" is defined herein as a peptide sequence usually present at the N-terminal end of newly synthesized secretory or membrane polypeptides which directs the polypeptide across or into a cell membrane of the cell (the plasma membrane in prokaryotes and the endoplasmic reticulum membrane in eukaryotes). It is usually subsequently removed. In particular a signal peptide may be capable of directing the polypeptide into a cell's secretory pathway.

The terms "subject," "patient," "individual," and the like as used herein are not intended to be limiting and can be generally interchanged. That is, an individual described as a "patient" does not necessarily have a given disease, but may be merely seeking medical advice.

The term "subject" as used herein includes an individual diagnosed with an ocular neurodegenerative disorder. For example, the individual is diagnosed with glaucoma.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. Treating also encompasses the prevention or amelioration of any symptom or symptoms of the disorder. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

In various embodiments, an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

As used herein, unless otherwise indicated, the terms "peptide", "polypeptide" or "protein" are used interchangeably herein, and refer to a polymer of amino acids of varying sizes. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or be naturally occurring. This term also includes polypeptides that have been modified or derivatized, such as by glycosylation, acetylation, phosphorylation, and the like.

As used in this specification and the appended claims, the term "or" is generally employed in its sense including "and/or" unless the content clearly dictates otherwise.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g. derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radio-isotope, fluorescent, and enzyme label.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In preferred embodiments, the genes, nucleic acid sequences, amino acid sequences, peptides, polypeptides and proteins are human.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An engineered vascular endothelial growth factor (VEGF) chimeric polypeptide comprising: a first VEGF polypeptide covalently linked to a second VEGF polypeptide via a first polypeptide linker comprising the amino acid sequence of SEQ ID NO: 14, and a second polypeptide linker comprising the amino acid sequence of SEQ ID NO: 15 linking the second VEGF polypeptide to a flexible transmembrane anchor.

2. The engineered VEGF chimeric polypeptide of claim 1, wherein the flexible transmembrane anchor is a glycosylphosphatidylinisotol (GPI) anchor.

3. The engineered VEGF chimeric polypeptide of claim 1, further comprising a signal peptide.

4. The engineered VEGF chimeric polypeptide of claim 1, wherein a signal peptide is linked to the N-terminal end of the first VEGF polypeptide.

5. The engineered VEGF chimeric polypeptide of claim 1, wherein each of the first and second VEGF polypeptides comprises about 100 amino acids to about 200 amino acids.

6. The engineered VEGF chimeric polypeptide of claim 5, wherein each of the first and second VEGF polypeptides comprises about 121 amino acids.

7. The engineered VEGF chimeric polypeptide of claim 1, wherein the first and second VEGF polypeptide comprise: isoforms, mutants, variants, derivatives, active fragments of VEGF or combinations thereof.

8. The engineered VEGF chimeric polypeptide of claim 1, wherein each of the first and second VEGF polypeptides is a VEGF isoform comprising 121 amino acids.

9. The engineered VEGF chimeric polypeptide of claim 8, wherein the VEGF isoform comprises the amino acid sequence set forth as SEQ ID NO: 13.

10. The engineered VEGF chimeric polypeptide of claim 1, wherein the flexible transmembrane anchor comprises SEQ ID NO: 6.

11. An engineered vascular endothelial growth factor (VEGF) chimeric polypeptide comprising: a sequence identity that is at least 80% identical to SEQ ID NO: 1 over the entire length of SEQ ID NO: 1.

12. The engineered VEGF chimeric polypeptide of claim 11, wherein the VEGF chimeric polypeptide comprises SEQ ID NO: 1.

13. The engineered vascular VEGF chimeric polypeptide of claim 11, further comprising a flexible peptide linker comprising about 7 amino acids.

14. The engineered vascular VEGF chimeric polypeptide of claim 11, wherein the VEGF polypeptide comprises about 189 amino acids.

15. A pharmaceutical composition comprising
the engineered vascular endothelial growth factor (VEGF) chimeric polypeptide of claim 1.

16. A retinal ganglion cell (RGC) comprising a membrane anchored vascular endothelial growth factor (VEGF) chimeric polypeptide, wherein said chimeric VEGF polypeptide comprises SEQ ID NO: 1.

17. A stem cell comprising the engineered vascular endothelial growth factor (VEGF) chimeric polypeptide of claim 1.

* * * * *

UNITED STATES PATENT AND TRADEMARK OFFICE
CERTIFICATE OF CORRECTION

| | | |
|---|---|---|
| PATENT NO. | : 12,404,312 B2 | Page 1 of 1 |
| APPLICATION NO. | : 16/978177 | |
| DATED | : September 2, 2025 | |
| INVENTOR(S) | : Yin-Shan Eric Ng and Junhui Shen | |

It is certified that error appears in the above-identified patent and that said Letters Patent is hereby corrected as shown below:

In the Claims

In Column 55, Lines 25-26 (approx.), Claim 2, delete "glycosylphosphatidylinisotol" and insert -- glycosylphosphatidylinositol --

In Column 56, Line 28, Claim 13, after "engineered" delete "vascular"

In Column 56, Line 31, Claim 14, after "engineered" delete "vascular"

Signed and Sealed this
Fourth Day of November, 2025

John A. Squires
*Director of the United States Patent and Trademark Office*